US010471125B2

(12) United States Patent
Huard et al.

(10) Patent No.: US 10,471,125 B2
(45) Date of Patent: Nov. 12, 2019

(54) PHARMACEUTICAL COMPOSITIONS AND THEIR USE FOR THE TREATMENT OF AUTOIMMUNE DISORDERS

(71) Applicant: UNIVERSITE GRENOBLE ALPES, Saint Martin d'Heres (FR)

(72) Inventors: Bertrand Huard, Grenoble (FR); Patrice Lalive, Chene-Bougeries (CH)

(73) Assignee: UNIVERSITE GRENOBLE ALPES, Grenoble (FR)

(*) Notice: Subject to any disclaimer, the term of this patent is extended or adjusted under 35 U.S.C. 154(b) by 76 days.

(21) Appl. No.: 15/118,337

(22) PCT Filed: Mar. 13, 2015

(86) PCT No.: PCT/EP2015/055371
§ 371 (c)(1),
(2) Date: Aug. 11, 2016

(87) PCT Pub. No.: WO2015/136108
PCT Pub. Date: Sep. 17, 2015

(65) Prior Publication Data
US 2017/0128536 A1    May 11, 2017

(30) Foreign Application Priority Data
Mar. 13, 2014 (EP) .................................. 14305362

(51) Int. Cl.
*A61K 38/19* (2006.01)
*C07K 14/52* (2006.01)
*C07K 14/525* (2006.01)
*A61K 38/17* (2006.01)
*A61K 9/00* (2006.01)
*C07K 14/47* (2006.01)

(52) U.S. Cl.
CPC .......... *A61K 38/191* (2013.01); *A61K 9/0019* (2013.01); *A61K 38/395* (2013.01); *C07K 14/47* (2013.01); *C07K 14/525* (2013.01); *C07K 2319/20* (2013.01); *C07K 2319/30* (2013.01)

(58) Field of Classification Search
CPC .. A61K 38/00; A61K 38/191; A61K 38/1709; A61K 38/17; A61K 38/19; C07K 14/525; C07K 14/47; C07K 14/435; C07K 14/46; C07K 14/52
See application file for complete search history.

(56) References Cited

U.S. PATENT DOCUMENTS 6,506,882 B2 * 1/2003 Yu ...................... C07K 16/2875
435/320.1

OTHER PUBLICATIONS

"Alzheimer's disease", ninds.nih.gov/disorders/alzheimersdisease/alzheimersdisease.htm; Jan. 4, 2012; 3 total pages.*
Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Chasset et al. APRIL levels are associated with disease activity in human chronic graft-versus-host disease. Heamatol 101: e312, 2016 (4 total pages).*
Cuny, G.D. Neurodegenerative diseases: challenges and opportunities. Future Med Chem 4(13): 1647-1649, 2012.*
Doerks et al. Protein annotation: detective work for function prediction. Trends in Genetics 14(6): 248-250, 1998.*
Elgert, K. Immunology, understanding the immune system. New York: Wiley-Liss, Inc., 1996; pp. 305, 324-326.*
Ngo et al. Computational complexity, protein structure prediction, and the Levinthal paradox. The Protein Folding Problem and Tertiary Structure Prediction, pp. 492-495, 1994.*
Samy et al. Targeting BAFF and APRIL in systemic lupus erythematosus and other antibody-associated diseases. Int Rev Immunol 36(1): 3-19, 2017.*
Shaker et al. Expression of TNFalpha, April, and BCMA in Behcet's disease. J Immunol Res 2014: 380405, 2014.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells. J.A. Additivity of mutational effects in proteins. Biochemistry 29 (37): 8509-8517, 1990.*
Baert et al. The role of APRIL—a proliferation inducing ligand—in autoimmune diseases and expectations from its targeting. J Autoimmunity 95: 179-190, 2018.*
Baert et al. A proliferation-inducing ligand-mediated anti-inflammatory response of astrocytes in multiple sclerosis. Ann Neurol 85: 406-420, 2019.*
Schwaller, Juerg, et al: "Neutrophil-derived APRIL concentrated in tumor lesions by proteoglycans correlates with human B-cell lymphoma aggressiveness", Blood, American Society of Hematology, US, vol. 109, No. 1, Jan. 1, 2007 (Jan. 1, 2007), pp. 331-338, XP002557376, ISSN: 0006-4971, [retrieved on Sep. 5, 2006], DOI: 10.1182/BLOOD-2006-02-001800.

(Continued)

Primary Examiner — Bridget E Bunner
(74) Attorney, Agent, or Firm — Young & Thompson

(57) ABSTRACT

A pharmaceutical composition in which the active substance includes or is: (i) a protein including the sequence SEQ ID NO: 1, representing the APRIL protein, (ii) any derived protein, which is derived from protein of sequence SEQ ID NO: 1 by substitution, removal or addition of one or more amino-acids, provided it allows the binding of the derived protein to an astrocyte and/or CSPG, (iii) any homologous protein, the sequence of which has a percentage of identity of at least approximately 70%, and in particular 85% with the sequence SEQ ID NO: 1, provided it allows the binding of the homologous protein to an astrocyte and/or CSPG, or (iv) any fragment of the protein of sequence SEQ ID NO: 1, provided it allows the binding of the fragment to an astrocyte and/or CSPG. The active substance is in association with an acceptable pharmaceutical vehicle.

5 Claims, 13 Drawing Sheets
Specification includes a Sequence Listing.

(56) References Cited

OTHER PUBLICATIONS

Huard, Bertrand, et al: "APRIL secreted by neutrophils binds to heparan sulfate proteoglycans to create plasma cell niches in human mucosa", Journal of Clinical Investigation, vol. 118, No. 8, Aug. 2008 (Aug. 1, 2008), pp. 2887-2895, XP002727709, ISSN: 0021-9738.

Kimberley, Fiona, et al: "APRIL in B-cell Malignancies and Autoimmunity", Death Receptors and Cognate Ligands in Cancer Springer-Verlag Berlin, Heidelberger Platz 3, D-14197 Berlin, Germany Series : Results and Problems in Cell Differentiation (ISSN 0080-1844(Print)), 2009, pp. 161-182, XP009179270.

Thangarajh, Mathula, et al: "Increased levels of APRIL (A Proliferation-Inducing Ligand) mRNA in multiple sclerosis", Journal of Neuroimmunology, Elsevier Science Publishers BV, NL, vol. 167, No. 1-2, Oct. 1, 2005 (Oct. 1, 2005), pp. 210-214, XP027673139, ISSN: 0165-5728, [retrieved on Oct. 1, 2005].

Thangarajh, Mathula, et al: "A Proliferation-inducing Ligand (APRIL) is Expressed by Astrocytes and is Increased in Multiple Sclerosis", Scandinavian Journal of Immunology, vol. 65, No. 1, Jan. 1, 2007 (Jan. 1, 2007), pp. 92-98, XP055130814, ISSN: 0300-9475, DOI: 10.1111/j.1365-3083.2006.01867.x.

Jagessar, S. Anwar, et al: "Antibodies Against Human BLyS and APRIL Attenuate EAE Development in Marmoset Monkeys", Journal of Neuroimmune Pharmacology, Kluwer Academic Publishers—Plenum Publishers, NE, vol. 7, No. 3, Jun. 30, 2012 (Jun. 30, 2012), pp. 557-570, XP035099224, ISSN: 1557-1904, DOI: 10.1007/S11481-012-9384-X.

Huntington, Nicholas D., et al: "A BAFF antagonist suppresses experimental autoimmune encephalomyelitis by targeting cell-mediated and humoral immune responses", International Immunology, vol. 18, No. 10, Aug. 7, 2006 (Aug. 7, 2006), pp. 1473-1485, XP055122652, ISSN: 0953-8178, DOI: 10.1093/intimm/dxl080.

Hartung, H.-P.: "Atacicept: a new B lymphocyte-targeted therapy for multiple sclerosis", Der Nervenarzt, vol. 80, No. 12, Sep. 26, 2009 (Sep. 26, 2009), pp. 1462-1472, XP055130895, ISSN: 0028-2804, DOI: 10.1007/s00115-009-2838-6.

Dumont, Jennifer, et al: "Monomeric FC Fusions: Impact on Pharmacokinetic and Biological Activity of Protein Therapeutics", Biodrugs: Clinical Immunotherapeutics, Biopharmaceuticals and Gene Therapy, Adis International, FR, vol. 20, No. 3, Jan. 1, 2006 (Jan. 1, 2006), pp. 151-160, XP009082835, ISSN: 1173-8804, DOI: 10.2165/00063030-200620030-00002.

International Search Report, dated May 13, 2015, from corresponding PCT Application.

European Search Report, dated Aug. 18, 2014, from corresponding European Application.

* cited by examiner

Figure 7B

|  | | HSPG binding | Valency |
|---|---|---|---|
| APRIL A$_{88}$ | .AVLTQ⬛Q⬛Q⬛SVLHLV... | yes | 3 |
| APRIL H$_{98}$ | ⬛SVLHLV... | no | 3 |

Figure 8B

| | | | HSPG binding | Valency |
|---|---|---|---|---|
| Mega-APRIL $A_{88}$ | ACRP30 | — A V L T Q K Q K K Q H S V L H L V ... | yes | 6 |
| Mega-APRIL $H_{98}$ | ACRP30 | — H S V L H L V ... | no | 6 |
| Fc-APRIL $A_{88}$ | Fcγ1 | — A V L T Q K Q K K Q H S V L H L V ... | yes | 6 |
| Fc-APRIL $H_{98}$ | Fcγ1 | — H S V L H L V ... | no | 6 |

PHARMACEUTICAL COMPOSITIONS AND THEIR USE FOR THE TREATMENT OF AUTOIMMUNE DISORDERS

The present invention relates to new pharmaceutical compositions and their use for the treatment of autoimmune disorders.

Multiple Sclerosis (MS) is one of the most common causes of neurologic disability in young adults with a huge impact on the quality of life and societal costs.

Multiple Sclerosis is an immune-mediated, demyelinating and neurodegenerative disease. The etiology is currently unknown and its pathogenesis is only partly understood. Complex genetic traits as well as environmental factors determine the susceptibility to develop the disease.

Remarkable progress has been made with regard to Multiple Sclerosis therapeutic treatment. Indeed, many disease-modifying therapies emerged that improve patient outcomes[1].

Nowadays, humoral immunity is thought to play an important role in the inflammatory response and development of demyelinated lesions.

Intrathecal antibody production is a hallmark of multiple sclerosis.

Indeed, histopathological studies have revealed prominent deposition of immunoglobulins and complement activation in some acute demyelinating lesions[2]. This group of patients (patients with MS and intrathecal antibody production) experienced a good response to therapeutic plasma exchange.

Moreover, the recent identification of lymphoid follicle-like structures in the cerebral meninges of some multiple sclerosis patients indicates that B-cell maturation can be sustained locally within the Central Nervous System (CNS), even if the detrimental or beneficial role of these structures is not yet fully discriminated.

Finally, depletion of B cells by therapeutic monoclonal antibody (RITUXIMAB®, a chimeric monoclonal antibody against the protein CD20, commercialized by Hoffman-La Roche and Genentech) has an effect on inflammatory activity in patients with Multiple Sclerosis[3], and recently, antibodies directed against the potassium channel Kir 4.1 has been identified in a large subset of Multiple Sclerosis patients. It would therefore seem that, at least in a subgroup of patients with multiple sclerosis, B cells and antibodies contribute substantially to the disease.

Extensive tissue experimentation has also permit to characterize a key function for APRIL at the level of plasma-cell survival in the bone marrow[4] and the inflamed mucosa[5].

A proliferation inducing ligand (APRIL), also known as Tall-1 or TNFSF13, is the last cloned member of the tumor necrosis factor family[6]. APRIL has two canonical signalling receptors, the B-cell maturation antigen (BCMA) and the transmembrane activator and CAML interactor (TACI)[7], almost exclusively expressed by B cells, thus explaining the specific function of APRIL at the level of humoral immunity[8]. APRIL is produced by myeloid cells[9]. Quite unique among the TNF superfamily but common for growth factors, heparan sulphate proteoglycans (HSPG) constitute coreceptors for APRIL[10], rendering the trimeric soluble form of APRIL active for receptor signalling by oligomerization[11].

As a plasma-cell survival factor, extensive investigations have been carried out worldwide to study the role of APRIL in autoimmunity, including multiple sclerosis.

At the level of APRIL expression in Multiple Sclerosis, the cerebrospinal fluids and sera of a small cohort (n=30) of newly diagnosed and untreated patients revealed no APRIL upregulation compared to control non inflammatory neurodegenerative disorders[12].

In Multiple Sclerosis lesions, it was also reported that astrocytes produce APRIL[13]. In fact, APRIL is indeed present in Multiple Sclerosis lesions but the authors misconcluded their report.

More and more brain functions are devoted to the astrocyte, including structural and metabolic support, blood-brain barrier formation/function, regulation of cerebral blood flow, clearance of neurotransmitters at the synapses, ion balance maintenance and myelination support[14]. The role of astrocyte in neuroinflammatory diseases has been recently highlighted, notably in neuromyelitis optica (NMO)[14].

APRIL antagonism in preclinical Multiple Sclerosis has also been tested.

In early 2006, a soluble form of BCMA, antagonist of APRIL and the related B-cell activation factor from the TNF family (BAFF) was reported to inhibit murine experimental autoimmune encephalitis (EAE)[15].

Recently, an antibody to APRIL was reported to specifically delay induction of EAE in primates[16].

Both study concluded to a reduction of the immune responses raised against the priming peptide from myelin oligodendrocyte glycoprotein (MOG) (vaccination with the MOG peptide induces an autoimmune responses conducting to demyelination of nerves in the central nervous system).

A big surprise came when such approaches were translated to Multiple Sclerosis patients. The clinical trial ATAMS (ATACICEPT in Multiple Sclerosis) consisted in the treatment of relapsing MS patients with a soluble form of TACI (also an antagonist of BAFF and APRIL). ATACICEPT is a recombinant fusion protein designed to inhibit B cells, thereby suppressing autoimmune disease. Indeed, B-cell depletion was well achieved with ATACICEPT in Multiple Sclerosis patients, but the trial was halted very rapidly due to an unexpected CNS inflammation exacerbation[17].

Thus, despite remarkable progress with regard to Multiple Sclerosis therapeutic treatment, none seems to be fully efficient. Indeed, continued relapses and eventual disability are still expected in the majority of patients on available therapies.

Thus, there is a need for a new treatment of autoimmune disorders, notably Multiple Sclerosis, which is more efficient than those of the prior art.

There is also a need for a new prevention of autoimmune disorders, notably Multiple Sclerosis.

There is also a need for a new treatment and/or prevention of autoimmune disorders, notably Multiple Sclerosis, which permits to avoid continued relapses and disability for patients with such autoimmune disorders, notably Multiple Sclerosis.

That is why, one of the aims of the invention is to provide new pharmaceutical compositions, useful for the prevention and/or treatment of autoimmune disorders, notably Multiple Sclerosis, more efficient than the pharmaceutical compositions used in the prior art.

Another aim of the invention is to provide new pharmaceutical compositions, useful for the prevention and/or treatment of autoimmune disorders, notably Multiple Sclerosis, which permits to avoid continued relapses and disability for patients with such autoimmune disorders, notably Multiple Sclerosis.

Another aim of the invention is to provide new chimeric proteins, and their use for the prevention and/or treatment of autoimmune disorders, notably Multiple Sclerosis.

Thus, the present invention concerns pharmaceutical compositions comprising as an active substance the APRIL protein or a nucleotidic sequence coding for an APRIL protein.

The present invention also concerns chimeric proteins comprising an APRIL protein.

The present invention also concerns compositions comprising as an active substance the APRIL protein or a nucleotidic sequence coding for an APRIL protein or a chimeric protein comprising an APRIL protein, for its use as a drug.

The present invention also concerns compositions comprising as an active substance the APRIL protein or a nucleotidic sequence coding for an APRIL protein or a chimeric protein comprising an APRIL protein, for its use for the manufacture of a drug for the prevention or the treatment of an autoimmune disorder.

The present invention also concerns compositions comprising as an active substance the APRIL protein or a nucleotidic sequence coding for an APRIL protein or a chimeric protein comprising an APRIL protein, for its use for the prevention or the treatment of an autoimmune disorder.

The invention relies on the unexpected experimental results according to which APRIL may protect mice from experimental autoimmune encephalitis.

Moreover, the invention also relies on human studies demonstrating that APRIL is greatly upregulated in lesions from Multiple Sclerosis patients, and that the secreted form of APRIL specifically binds to reactive astrocytes in lesions.

The invention also relies on human studies demonstrating that the secreted form of APRIL binds to Chondroitin Sulfate ProtcoGlycans (CSPG) in the surrounding astroglial scar rich in the said CSPG (in the extracellular matrice). In this structure, CSPG inhibit neural self-regeneration following trauma in the central nervous system[21].

In fact, the invention relies on the fact that APRIL may have some neuroprotective activities. More precisely, the invention relies on the fact that APRIL may have some neuroprotective activities by binding to astrocytes and/or by interfering with the anti-regenerative process mediated by CSPG (that is to say by binding to CSPG).

Thus, in a first embodiment, the present invention relates to a pharmaceutical composition wherein the active substance comprises or consists in:
  a protein comprising the sequence SEQ ID NO: 1, representing the APRIL protein,
  or any derived protein, which is derived from protein of sequence SEQ ID NO: 1 by substitution, removal or addition of one or more amino-acids, provided it allows the binding of the said derived protein to an astrocyte,
  or any homologous protein, the sequence of which has a percentage of identity of at least approximately 70%, and in particular 85% with said sequence SEQ ID NO: 1, provided it allows the binding of the said homologous protein to an astrocyte,
  or any fragment of the protein of sequence SEQ ID NO: 1, provided it allows the binding of the said fragment to an astrocyte,
in association with an acceptable pharmaceutical vehicle.

In another embodiment, the present invention relates to a pharmaceutical composition wherein the active substance comprises or consists in:
  a protein comprising the sequence SEQ ID NO: 1, representing the APRIL protein,
  or any derived protein, which is derived from protein of sequence SEQ ID NO: 1 by substitution, removal or addition of one or more amino-acids, provided it allows the binding of the said derived protein to CSPG,
  or any homologous protein, the sequence of which has a percentage of identity of at least approximately 70%, and in particular 85% with said sequence SEQ ID NO: 1, provided it allows the binding of the said homologous protein to CSPG,
  or any fragment of the protein of sequence SEQ ID NO: 1, provided it allows the binding of the said fragment to CSPG,
in association with an acceptable pharmaceutical vehicle.

APRIL protein is a transmembrane protein undergoing cleavage by furin protase in order to be secreted[15]. Furin protease cleaves before the Alanine at position 88 (see the SEQ ID NO: 3 which is the complete sequence of APRIL protein).

Thus, secreted APRIL is from amino acid 88 (an alanine) to amino acid 233 (a leucine).

Thus, APRIL part remaining anchored at the membrane after furin processing is from amino acid 1 (a methionine) to amino acid 87 (an arginine).

Secreted APRIL and APRIL part remaining anchored at the membrane are shown in FIG. 1.

SEQ ID NO: 1 is the following sequence in amino acids:

```
HSVLHLVPINATSKDDSDVTEVMWQPALRRGRGLQAQGYGVRIQDAGV
YLLYSQVLFQDVTFTMGQVVSREGQGRQETLFRCIRSMPSHPDRAYNS
CYSAGVFHLHQGDILSVIIPRARAKLNLSPHGTFLGFVKL
```

SEQ ID NO: 1 corresponds to the secreted APRIL protein, also named APRIL $H_{98}$ because it is constituted by the sequence from amino acid 98 (a histidine) to amino acid 233 (a leucine) of the sequence of the full-length APRIL protein (see SEQ ID NO: 3). This secreted APRIL protein does not possess HSPG binding domains. HSPG (Heparan Sulphate ProteoGlycans) acts as coreceptor ensuring oligomerization of soluble APRIL to optimally signal via APRIL known receptors (TACI and BCMA).

APRIL is as all the TNF like molecules produced as a trimer and the active soluble APRIL is at least a dimer of this trimer.

According to the invention, the expression "the sequence of which has a percentage of identity of at least approximately 70%" means that the percentage of identity can be 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Astrocytes are characteristic star-shaped glial cells in the brain and spinal cord. They are the most abundant cells of the human brain and they perform many functions such as structural and metabolic support, blood-brain barrier formation/function, regulation of cerebral blood flow, clearance of neurotransmitters at the synapses, ion balance maintenance and myelination support.

Chondroitin sulfate proteoglycans (CSPG) are proteoglycans consisting of a protein core and a chondroitin sulfate side chain. They are structural components of a variety of human tissues, including cartilage. They also play key roles in neural development and glial scar formation. Notably, CSPG are known to inhibit axon regeneration after spinal cord injury, and they are known to contribute to glial scar formation post injury, acting as a barrier against new axons growing into the injury site.

CSPG are also ligands for the inhibitory receptors: NogoR1, NogoR3 and protein tyrosine phosphatase sigma.

APRIL can bind to one or several CSPG in central nervous system (CNS), including aggrecan, brevican, neurocan, phosphocan, keratane sulfate proteoglycan, neuroneglial antigen2. APRIL has the potential to bind to all these CSPG.

An acceptable pharmaceutical vehicle can be any kind of physiological solutions.

In another embodiment, the invention relates to a pharmaceutical composition wherein the active substance comprises or consists in:
- a protein comprising the sequence SEQ ID NO: 2, representing the APRIL protein,
- or any derived protein, which is derived from protein of sequence SEQ ID NO: 2 by substitution, removal or addition of one or more amino-acids, provided it allows the binding of the said derived protein to an astrocyte,
- or any homologous protein, the sequence of which has a percentage of identity of at least approximately 70%, and in particular 85% with said sequence SEQ ID NO: 2, provided it allows the binding of the said homologous protein to an astrocyte,
- or any fragment of the protein of sequence SEQ ID NO: 2, provided it allows the binding of the said fragment to an astrocyte, in association with an acceptable pharmaceutical vehicle.

In another embodiment, the invention relates to a pharmaceutical composition wherein the active substance comprises or consists in:
- a protein comprising the sequence SEQ ID NO: 2, representing the APRIL protein,
- or any derived protein, which is derived from protein of sequence SEQ ID NO: 2 by substitution, removal or addition of one or more amino-acids, provided it allows the binding of the said derived protein to CSPG,
- or any homologous protein, the sequence of which has a percentage of identity of at least approximately 70%, and in particular 85% with said sequence SEQ ID NO: 2, provided it allows the binding of the said homologous protein to CSPG,
- or any fragment of the protein of sequence SEQ ID NO: 2, provided it allows the binding of the said fragment to CSPG, in association with an acceptable pharmaceutical vehicle.

SEQ ID NO: 2 is the following sequence in amino acids:

```
AVLTQKQKKQHSVLHLVPINATSKDDSDVTEVMWQPALRRGRGLQA

QGYGVRIQDAGVYLLYSQVLFQDVTFTMGQVVSREGQGRQETLFRC

IRSMPSHPDRAYNSCYSAGVFHLHQGDILSVIIPRARAKLNLSPHG

TFLGFVKL
```

SEQ ID NO: 2 corresponds to the secreted APRIL protein which possess an HSPG binding domain which is KQKQH.

Secreted APRIL protein which possesses an HSPG binding domain is also named APRIL $A_{88}$ because it is constituted by the sequence from amino acid 88 (an alanine) to amino acid 233 (a leucine) of the sequence of the full-length APRIL protein (see SEQ ID NO: 3)

HSPG binding domain is situated among the first ten amino acids of the SEQ ID NO: 2. It is underlined in SEQ ID NO: 2. Thus, SEQ ID NO: 2 contains only the following supplementary amino acids in comparison with SEQ ID NO: 1 (AVLTQKOKK).

A test for checking the binding between the secreted APRIL protein and an astrocyte can be the following test:
- Immunostain CRT-MG astrocytes with Fc control and Fc-APRILA$_{88}$ (1 µg/ml) or control Fas-Fc (1 µg/ml) for 30 minutes at 4 C in PBS 1% BSA;
- Wash cells;
- Incubate cells with Alexa488-conjugated human Ig antiserum for another 30 minutes at 4° C.;
- Wash cells;
- Resuspend in PBS;
- Analyse fluorescence with the LSRII Becton Dickinson flow cytometer.

CRT-MG is a human astrocyte cell line.

Fc-APRILA$_{88}$ is the fragment of secreted APRIL which begins at amino acid A88 (an alanine) of the sequence of the full-length APRIL protein (see SEQ ID NO: 3) linked with a Fc fragment from a human immunoglobulin. This link is carried out by genetic engineering. That is why this link it is a covalent bound.

Fas-Fe is used here as an irrelevant control for putative binding via Fc receptors. The extracellular domain of Fas was linked to the same Fc fragment.

A test for checking the binding between APRIL and CSPG can be the following test:
- Preincubate Fc-APRILA$_{88}$ (1 µg/ml) with or without CSPG for 30 minutes at 4 C in PBS 1% BSA;
- Immunostain CRT-MG astrocytes for 30 minutes at 4° C.;
- Wash cells;
- Incubate cells with Alexa488-conjugated human Ig antiserum for another 30 minutes at 4 C;
- Wash cells;
- Resuspend in PBS;
- Analyse fluorescence with the LSRII Becton Dickinson flow cytometer.

In another embodiment, the invention relates to a pharmaceutical composition wherein the active substance comprises or consists in:
- a protein comprising the sequence SEQ ID NO: 3, representing the APRIL protein,
- or any derived protein, which is derived from protein of sequence SEQ ID NO: 3 by substitution, removal or addition of one or more amino-acids, provided it allows the binding of the said derived protein to an astrocyte,
- or any homologous protein, the sequence of which has a percentage of identity of at least approximately 70%, and in particular 85% with said sequence SEQ ID NO: 3, provided it allows the binding of the said homologous protein to an astrocyte,
- or any fragment of the protein of sequence SEQ ID NO: 3, provided it allows the binding of the said fragment to an astrocyte, in association with an acceptable pharmaceutical vehicle.

In another embodiment, the invention relates to a pharmaceutical composition wherein the active substance comprises or consists in:
- a protein comprising the sequence SEQ ID NO: 3, representing the APRIL protein,
- or any derived protein, which is derived from protein of sequence SEQ ID NO: 3 by substitution, removal or addition of one or more amino-acids, provided it allows the binding of the said derived protein to CSPG,
- or any homologous protein, the sequence of which has a percentage of identity of at least approximately 70%, and in particular 85% with said sequence SEQ ID NO: 3, provided it allows the binding of the said homologous protein to CSPG, or any fragment of the protein of sequence SEQ ID NO: 3, provided it allows the binding of the said fragment to CSPG, in association with an acceptable pharmaceutical vehicle.

SEQ ID NO: 3 is the following sequence in amino acids:

MGGPVREPALSVALWLSWGAALGAVACAMALLTQQTELQSLRREVSRLQG

TGGPSQNGEGYPWQSLPEQSSDALEAWENGERSRKRRAVLTQKQKKQHSV

LHLVPINATSKDDSDVTEVMWQPALRRGRGLQAQGYGVRIQDAGVYLLYS

QVLFQDVTFTMGQVVSREGQGRQETLFRCIRSMPSHPDRAYNSCYSAGVF

HLHQGDILSVIIPRARAKLNLSPHGTFLGFVKL

SEQ ID NO: 3 corresponds to the sequence of the full-length human APRIL protein.

In another embodiment, the invention relates to a pharmaceutical composition wherein the active substance comprises or consists in:
- a nucleotidic sequence coding for a protein comprising SEQ ID NO: 1 or a nucleotidic sequence of SEQ ID NO: 4, coding for a protein having the sequence SEQ ID NO: 1,
- or any derived nucleotidic sequence, by degeneration of code genetic, of sequence SEQ ID NO: 4,
- or any derived nucleotidic sequence, by substitution, suppression or addition of one or more nucleotides, of sequence SEQ ID NO: 4.
- or any homologous nucleotidic sequence having a percentage of identity of at least approximately 70%, with sequence SEQ ID NO: 4,
- or any fragment of nucleotidic sequence SEQ ID NO: 4 or of the above defined nucleotidic sequences, the aforementioned fragment preferably making up of at least approximately 20 contiguous nucleotides in the aforementioned sequence.

The expression "a nucleotidic sequence coding for a protein comprising SEQ ID NO: 1" means for example a nucleotidic sequence coding for a fusion protein comprising the secreted APRIL protein corresponding to SEQ ID NO: 1.

The nucleotidic sequence of SEQ ID NO: 4, coding for a protein having the sequence SEQ ID NO: 1, is the following:

cactctgtcctgcacctggttcccattaacgccacctccaaggatgact ccgatgtgacagaggtgatgtggcaaccagctcttaggcgtgggagagg cctacaggcccaaggatatggtgtccgaatccaggatgctggagtttat ctgctgtatagccaggtcctgtttcaagacgtgactttcaccatgggtc aggtggtgtctcgagaaggccaaggaaggcaggagactctattccgatg tataagaagtatgccctcccacccggaccgggcaacaaeagctgctata gcgcaggtgtcttccatttacaccaaggggatattctgagtgtcataat tccccGggcaagggcgaaacttaacctctctccacatggaaccttcctg gggtttgtgaaactgtga SEQ ID NO: 4 is the coding sequence (CDS) of human soluble APRIL H$_{98}$ of SEQ ID NO: 1.

In another embodiment, the invention relates to a pharmaceutical composition wherein the active substance comprises or consists in:
- a nucleotidic sequence coding for a protein comprising SEQ ID NO: 2 or a nucleotidic sequence of SEQ ID NO: 5, coding for a protein having the sequence SEQ ID NO: 2,
- or any derived nucleotidic sequence, by degeneration of code genetic, of sequence SEQ ID NO: 5,
- or any derived nucleotidic sequence, by substitution, suppression or addition of one or more nucleotides, of sequence SEQ ID NO: 5,
- or any homologous nucleotidic sequence having a percentage of identity of at least approximately 70%, with sequence SEQ ID NO: 5,
- or any fragment of nucleotidic sequence SEQ ID NO: 5 or of the above defined nucleotidic sequences, the aforementioned fragment preferably making up of at least approximately 20 contiguous nucleotides in the aforementioned sequence.

The expression "a nucleotidic sequence coding for a protein comprising SEQ ID NO: 2" means for example a nucleotidic sequence coding for a fusion protein comprising the secreted APRIL protein corresponding to SEQ ID NO: 2.

The nucleotidic sequence of SEQ ID NO: 5, coding for a protein having the sequence SEQ ID NO: 2, is the following:

gcagtgctcacccaaaaacagaagaagcagcactctgtcctgcacctgg ttcccattaacgccacctccaaggatgactccgatgtgacagaggtgat gtggcaaccagctcttaggcgtgggagaggcctacaggcccaaggatat ggtgtccgaatccaggatgctggagtttatctgctgtatagccaggtcc tgatcaagacgtgactttcaccatgggtcaggtggtgtctcgagaaggc caaggaaggcaggagactctattccgatgtaaagaagtatgccctccca cccggaccgggcctacaacagctgctatagcgcaggtgtcttccattta caccaaggggatattctgagtgtcataattccccGggcaagggcgaaac ttaacctctctccacatggaaccacctggggtagtcaaactgtga SEQ ID NO: 5 is the coding sequence (CDS) of human soluble APRIL A$_{88}$ of SEQ ID NO: 2.

In another embodiment, the invention relates to a pharmaceutical composition wherein the active substance comprises or consists in:
- a nucleotidic sequence coding for a protein comprising SEQ ID NO: 3 or a nucleotidic sequence of SEQ ID NO: 6, coding for a protein having the sequence SEQ ID NO: 3,
- or any derived nucleotidic sequence, by degeneration of code genetic, of sequence SEQ ID NO: 6,
- or any derived nucleotidic sequence, by substitution, suppression or addition of one or more nucleotides, of sequence SEQ ID NO: 6,
- or any homologous nucleotidic sequence having a percentage of identity of at least approximately 70%, with sequence SEQ ID NO: 6,
- or any fragment of nucleotidic sequence SEQ ID NO: 6 or of the above defined nucleotidic sequences, the aforementioned fragment preferably making up of at least approximately 20 contiguous nucleotides in the aforementioned sequence.

The expression "a nucleotidic sequence coding for a protein comprising SEQ ID NO: 3" means for example a nucleotidic sequence coding for a fusion protein comprising the secreted APRIL protein corresponding to SEQ ID NO: 3.

The nucleotidic sequence of SEQ ID NO: 6, coding for a protein having the sequence SEQ ID NO: 3, is the following:

atgggggggcccagtcagagagccggcactctcagttgccctctggttgag ttgggggggcagctaggggggccgtggcttgtgccatggctagctgacccaa

```
caaacagagctgcagagcctcaggagagaggtgagccggctgcaggggac aggaggcccctcccagaatggggaagggtatccctggcagagtctcccgg agcagagttccgatgccctggaagcctgggagaatggggagagatcccgg aaaaggagagcagtgctcacccaaaaacagaagaagcagcactctgtcct gcacctggacccattaacgccacctccaaggatgactccgatgtcacaga ggtgatgAggcaaccagctcttaggcgtgggagaggcctacaggcccaag gatatggtgtccgaatccaggatgctggagtttatctcctgtatagccag gtcctgtttcaagacgtgactttcaccatcggtcaggtggtgtctcgaga aggccaagcaacccaggagactctattccgatgtataagaagtatgccct cccaccoggaccgggcctacaacagctgctatagcgcaggtgtcttccat ttacaccaaggggatattctcagtgtcataattccccgggcaagggcgaa acttaacctctctccacatggaaccttcctcgggtagtgaaactgtga
```

SEQ ID NO: 6 is the coding sequence (CDS) of full-length human APRIL of SEQ ID NO: 3.

In another embodiment, in the pharmaceutical composition according to the invention, the active substance comprises or consists in a vector in particular, plasmid, cosmid, phage or DNA of virus, containing a sequence as described in SEQ ID NO: 4 or SEQ ID NO: 5 or SEQ ID NO: 6.

In a particular embodiment, in the pharmaceutical composition of the invention, the protein has the sequence SEQ ID NO: 1.

In a particular embodiment, in the pharmaceutical composition of the invention, the protein has the sequence SEQ ID NO: 2.

In a particular embodiment, in the pharmaceutical composition of the invention, the protein has the sequence SEQ ID NO: 3.

In another embodiment, in the pharmaceutical composition of the invention, the protein is a chimeric protein constituted by an oligomer of the protein of sequence SEQ ID NO: 1, or a derived protein, or a homologous protein or a fragment of the sequence SEQ ID NO: 1, each protein or fragment being linked to the other by a constant region of an immunoglobulin.

An oligomer of the protein means at least two proteins or two fragments linked to the other by a constant region of an immunoglobulin.

An oligomer can be a dimer, a trimer, a multimer. As previously explained, in a particular embodiment the active protein is at least a dimer of trimer.

A chimeric protein can be produced by the methods known by the person having ordinary skill in the art, notably the methods of DNA subcloning.

A constant region of an immunoglobulin is the Fc fragment. In a preferred embodiment, a Fc fragment of a human immunoglobulin can be used. In another preferred embodiment, a Fc fragment of immunoglobulins IgG, IgA, or IgM can be used, in particular a Fc fragment of IgG1 which is represented by SEQ ID NO: 12.

SEQ ID NO: 12 is the following sequence:

```
PPCPAPELLGGPSVFLFPPKPKDTLMISRTPEVTCVVVDVSHEDPEVKFN

WYVDGVENHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK
```

It corresponds to the Fc portion of a human immunoglobulin G, from amino acid 108 to 329 of accession number AAC82527.

In another embodiment, in the pharmaceutical composition of the invention, the protein is a chimeric protein constituted by an oligomer of the protein of sequence SEQ ID NO: 2, or a derived protein, or a homologous protein or a fragment of the sequence SEQ ID NO: 2, each protein or fragment being linked to the other by a constant region of an immunoglobulin.

In another embodiment, in the pharmaceutical composition of the invention, the protein is a chimeric protein constituted by an oligomer of the protein of sequence SEQ ID NO: 3, or a derived protein, or a homologous protein or a fragment of the sequence SEQ ID NO: 3, each protein or fragment being linked to the other by a constant region of an immunoglobulin.

In another embodiment, in the pharmaceutical composition of the invention, the protein is a chimeric protein constituted by an oligomer of the protein of sequence SEQ ID NO: 1, or a derived protein, or a homologous protein or a fragment of the sequence SEQ ID NO: 1, each protein or fragment being linked to the headless region of a ACRP30 protein.

An oligomer of the protein means at least two proteins or two fragments linked to another by the headless region of a ACRP30 protein. An oligomer can also be a dimer, a trimer, a multimer.

ACRP30 protein is the Adipocyte Complement-Related Protein of 30 kD. The headless region of ACRP30 protein is represented by SEQ ID NO: 11.

SEQ ID NO: 11 is the following sequence:

```
HDQETTTQGPGVLLPLPKGACTGWMAGIPGHPGHNGAPGRDGRDGTPGE
KGEKGDPGLIGPKGDIGETGVPGAEGPRGFPGIQGRKGEPGEGA
```

More information about the Fc fragment and headless region of ACRP30 protein which can be used according to the present invention can be found in Holler et al., Molecular and Cellular Biology, February 2003, p 1428-1440.

In another embodiment, in the pharmaceutical composition of the invention, the protein is a chimeric protein constituted by an oligomer of the protein of sequence SEQ ID NO: 2, or a derived protein, or a homologous protein or a fragment of the sequence SEQ ID NO: 2, each protein or fragment being linked to the headless region of a ACRP30 protein.

In another embodiment, in the pharmaceutical composition of the invention, the protein is a chimeric protein constituted by an oligomer of the protein of sequence SEQ ID NO: 3, or a derived protein, or a homologous protein or a fragment of the sequence SEQ ID NO: 3, each protein or fragment being linked to the headless region of a ACRP30 protein.

In another embodiment, in the pharmaceutical composition of the invention, the active substance forms a complex with an astrocyte and/or with CSPG.

The expression "a complex with an astrocyte and/or with CSPG" means that the active substance can form a complex with only an astrocyte. It also means that the active substance can form a complex with an astrocyte and one or several CSPG. It also means that the active substance can form a complex with one or several CSPG.

The complex can be formed by one active substance and one astrocyte and/or CSPG or several active substances and one astrocyte and/or CSPG.

For example, the complex can be formed between one astrocyte and/or CSPG and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the other by a constant region of an immunoglobulin.

The complex can also be formed between one astrocyte and/or CSPG and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the headless region of a ACRP30 protein.

The complex can also be formed between one astrocyte and/or CSPG and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the other by a constant region of an immunoglobulin and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the headless region of a ACRP30 protein.

In a particular embodiment, the complex can be formed between one astrocyte and/or CSPG and one or several chimeric proteins MEGA-APRIL $A_{88}$.

In a particular embodiment, the complex can be formed between one astrocyte and/or CSPG and one or several chimeric proteins MEGA-APRIL $H_{98}$.

In a particular embodiment, the complex can be formed between one astrocyte and/or CSPG and one or several chimeric proteins MEGA-APRIL $A_{88}$ and one or several chimeric proteins MEGA-APRIL $H_{98}$.

In a particular embodiment, the complex can be formed between one astrocyte and/or CSPG and one or several chimeric proteins Fc-APRIL $A_{88}$.

In a particular embodiment, the complex can be formed between one astrocyte and/or CSPG and one or several chimeric proteins Fc-APRIL $H_{98}$.

In a particular embodiment, the complex can be formed between one astrocyte and/or CSPG and one or several chimeric proteins Fc-APRIL $A_{88}$ and one or several chimeric proteins Fc-APRIL $H_{98}$.

In a particular embodiment, the complex can be formed between one astrocyte and/or CSPG and one or several chimeric proteins MEGA-APRIL $A_{88}$ and one or several chimeric proteins Fc-APRIL $A_{88}$.

In a particular embodiment, the complex can be formed between one astrocyte and/or CSPG and one or several chimeric proteins MEGA-APRIL $A_{88}$ and one or several chimeric proteins Fc-APRIL $H_{98}$.

In a particular embodiment, the complex can be formed between one astrocyte and/or CSPG and one or several chimeric proteins MEGA-APRIL $H_{98}$ and one or several chimeric proteins Fc-APRIL $A_{88}$.

In a particular embodiment, the complex can be formed between one astrocyte and/or CSPG and one or several chimeric proteins MEGA-APRIL $H_{98}$ and one or several chimeric proteins Fc-APRIL $H_{98}$.

In a particular embodiment, the complex can be formed between one astrocyte and/or CSPG and one or several chimeric proteins Fc-APRIL $A_{88}$ and one or several chimeric proteins Fc-APRIL $H_{98}$ and one or several MEGA-APRIL $A_{88}$.

In a particular embodiment, the complex can be formed between one astrocyte and/or CSPG and one or several chimeric proteins Fc-APRIL $A_{88}$ and one or several chimeric proteins Fc-APRIL $H_{98}$ and one or several MEGA-APRIL $H_{98}$.

In a particular embodiment, the complex can be formed between one astrocyte and/or CSPG and one or several chimeric proteins MEGA-APRIL $A_{88}$ and one or several chimeric proteins MEGA-APRIL $H_{98}$ and one or several chimeric proteins Fc-APRIL $A_{88}$.

In a particular embodiment, the complex can be formed between one astrocyte and/or CSPG and one or several chimeric proteins MEGA-APRIL $A_{88}$ and one or several chimeric proteins MEGA-APRIL $H_{98}$ and one or several chimeric proteins Fc-APRIL $H_{98}$.

In a particular embodiment, the complex can be formed between one astrocyte and/or CSPG and one or several chimeric proteins MEGA-APRIL $A_{88}$ and one or several chimeric proteins MEGA-APRIL $H_{98}$ and one or several chimeric proteins Fc-APRIL $A_{88}$ and one or several chimeric proteins Fc-APRIL $H_{98}$.

In another particular embodiment, the complex can be formed by one active substance as defined above and one neuron or several active substances as defined above and one neuron.

In another particular embodiment, the complex can be formed by one active substance as defined above and one oligodendrocyte or several active substances as defined above and one oligodendrocyte.

In another embodiment, in the pharmaceutical composition of the invention, the protein of one of the sequences SEQ ID NO: 1 or SEQ ID NO: 2 or SEQ ID NO: 3 is the active substance which forms a complex with an astrocyte and/or with CSPG.

In another embodiment, in the pharmaceutical composition of the invention, the chimeric protein constituted by an oligomer of the protein of one of the sequences SEQ ID NO: 1 or SEQ ID NO: 2 or SEQ ID NO: 3, or a derived protein, or a homologous protein or a fragment of one of the sequences SEQ ID NO: 1 or SEQ ID NO: 2 or SEQ ID NO: 3, each protein or fragment being linked to the other by a constant region of an immunoglobulin, is the active substance which forms a complex with an astrocyte and/or with CSPG.

In another embodiment, in the pharmaceutical composition of the invention, the chimeric protein constituted by an oligomer of the protein of one of the sequences SEQ ID NO: 1 or SEQ ID NO: 2 or SEQ ID NO: 3, or a derived protein, or a homologous protein or a fragment of one of the sequences SEQ ID NO: 1 or SEQ ID NO: 2 or SEQ ID NO: 3, each protein or fragment being linked to the headless region of a ACRP30 protein, is the active substance which forms a complex with an astrocyte and/or with CSPG.

In another embodiment, in the pharmaceutical composition of the invention, the chimeric protein comprising or consisting in SEQ ID NO: 7 or SEQ ID NO: 8 or SEQ ID NO: 9 or SEQ ID NO: 10 is the active substance which forms a complex with an astrocyte and/or with CSPG.

In another embodiment, the present invention relates to a pharmaceutical composition, wherein the active substance is formulated for administration in a range of doses from about 0.1 mg/kg to about 20 mg/kg.

The expression "doses from about 0.1 mg/kg to about 20 mg/kg" means for example 0.1 mg/kg; 0.2 mg/kg; 0.3 mg/kg; 0.4 mg/kg; 0.4 mg/kg; 0.5 mg/kg; 0.6 mg/kg; 0.7 mg/kg; 0.8 mg/kg; 0.9 mg/kg; 1.0 mg/kg; 2.0 mg/kg; 3.0 mg/kg; 4.0 mg/kg; 5.0 mg/kg; 6.0 mg/kg; 7.0 mg/kg; 8.0 mg/kg; 9.0 mg/kg; 10.0 mg/kg; 11.0 mg/kg; 12.0 mg/kg; 13.0 mg/kg; 14.0 mg/kg; 15.0 mg/kg; 16.0 mg/kg; 17.0 mg/kg; 18.0 mg/kg; 19.0 mg/kg; 20.0 mg/kg.

In another embodiment, the pharmaceutical composition according to the present invention is administered by an intravenous injection or an intrathecal injection.

The pharmaceutical composition according to the present invention can also be administered by intranasal injection and intracerebroventricular injection.

The pharmaceutical composition according to the present invention can also contain any other active substances which are considered appropriate by the one with ordinary skill in the art, for example any drug which can be used for the prevention and/or the treatment of neurodegenerative diseases or autoimmune diseases.

In another embodiment, the pharmaceutical composition of the present invention can also contain the following active substances: Teriflunomide; Interferon Beta; Fingolimod; Alemtuzumab; Glatiramer acetate; Mitoxantrone; Dimethyl Fumarate; Natalizumab, notably if the said pharmaceutical composition is used for the prevention and/or the treatment of the multiple sclerosis or another autoimmune neurodegenerative disease (NDD).

In another embodiment, the pharmaceutical composition of the present invention can also contain the following active substance: Riluzole, notably if the said pharmaceutical composition is used for the prevention and/or the treatment of Amyotrophic Lateral Sclerosis.

In another embodiment, the pharmaceutical composition of the present invention can also contain cholinesterase inhibitors such as Donepezil; Galantamine; Rivastigmine, notably if the said pharmaceutical composition is used for the prevention and/or the treatment of Alzheimer disease In another embodiment, the pharmaceutical composition of the present invention can also contain substances which act on the dopamine pathway such as Levodopa; Pramipexole; Ropinirole, notably if the said pharmaceutical composition is used for the prevention and/or the treatment of Parkinson Disease.

In another embodiment, the pharmaceutical composition of the present invention can also contain the following active substances: Aripiprazole; Asenapine; Clozapine; Iloperidone; Lurasidone; Olanzapine; Paliperidone; Quetiapine; Risperidone; Ziprasidone; Chlorpromazine; Fluphenazine; Haloperido; Perphenazine, notably if the said pharmaceutical composition is used for the prevention and/or the treatment of Schizophrenia.

In a second embodiment, the present invention relates to chimeric proteins comprising or consisting in SEQ ID NO: 7 or SEQ ID NO: 8 or SEQ ID NO: 9 or SEQ ID NO: 10.

SEQ ID NO: 7 corresponds to the sequence of "MEGA-APRIL $A_{88}$ protein" and is constituted by:
  the sequence of the human ACRP30 headless which corresponds to SEQ ID NO: 11
  the sequence of the human APRIL $A_{88}$ which corresponds to SEQ ID NO: 2 SEQ ID NO: 7 corresponds to the following sequence:

HDQETTTQGPGVLLPLPKGACTGWMAGIPGHPGHNGAPGRDGRDTPGEK

GEKGDPGLIGPKGDIGETGVPGAEGPRGFPGIQGRKGEPGEGAAVLTQKQ

KKQHSVLHLVPINATSKDDSDVTEVMWQPALRRGRGLQAQGYGVRIQDAG

VYLLYSQVLFQDVTFTMGQVVSREGQGRQETLFRCIRSMPSHPDRAYNSC

YSAGVFHLHQGDILSVIIPRARAKLLSPHGTFLGFVKL

SEQ ID NO: 8 corresponds to the sequence of "MEGA-APRIL $H_{98}$ protein" and is constituted by:
  the sequence of the human ACRP30 headless which corresponds to SEQ ID NO: 11
  the sequence of the human APRIL $H_{98}$ which corresponds to SEQ ID NO: 1 SEQ ID NO: 8 corresponds to the following sequence:

HDQETTTQGPGVLLPLPKGACTGWNTAGIPGHPGHNGAPGRDGRDTPGE

KGEKGDPGLIGPKGDIGETGVPGAEGPRGFPGIQGRKGEPGEGAHSVLHL

VPINATSKDDSDVTEVMWQPALRRGRGLQAQGTGVRIQDAGVYLLYSQVL

FQDVTFTMGQVVSREGQGRQETLFRCIRSMPSHPDRAYNSCYSAGVFHLH

QGDILSVIIPRARAKLNLSPHGTFLGFVKL

SEQ ID NO: 9 corresponds to the sequence of "Fc-APRIL $A_{88}$ protein" and is constituted by:
  the sequence of the Fc portion of human immunoglobulin G which corresponds to SEQ ID NO: 12
  a linker sequence which corresponds to SEQ ID NO: 13
  the sequence of the human APRIL $A_{88}$ which corresponds to SEQ ID NO: 2 SEQ ID NO: 9 corresponds to the following sequence:

PPCPAPELLGGPSVFLFPPKPKDTLMISRTPEVTCVVVDVSHEDPEVKF

NWYNDGVEVHNAKTKPREEQYNSTYRVVSVLTVLHQDWLNGKEYKCKVS

NKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNV

FSCSVMHEALHNHYTQKSLSLSPGKRSPQPQPKPQPKPEPEGSLQAVLT

QKQKKQHSVLHLVPINATSKDDSDVTEVMWQPALRRGRGLQAQGYGVRI

QDAGVYLLYSQVLFQDVTFTMGQVVSREGQGRQETLFRCIRSMPSHPDR

AYNSCYSAGVFHLHQGDILSVIIPRARAKLNLSPHGTFLGFVKL

SEQ ID NO: 10 corresponds to the sequence of "Fc-APRIL $H_{98}$ protein" and is constituted by:
  the sequence of the Fc portion of human immunoglobulin G which corresponds to SEQ ID NO: 12
  a linker sequence which corresponds to SEQ ID NO: 13
  the sequence of the human APRIL $H_{98}$ which corresponds to SEQ ID NO: 1 SEQ ID NO: 10 corresponds to the following sequence:

PPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNV

FSCSVMHEALHNHYTQKSLSLSPGKRSPQPQPKPQPKPEPEGSLQHSVT

-continued

HLVPINATSKDDSDVTEVMWQPALRRGRGLQAQGYGVRIQDAGVYLLYS

QVLFQDVTFTMGQVVSREGQGRQETLFRCIRSMPSHPDRAYNSCYSAGV

FHLHQGDILSVIIPRARAKLNLSPHGTFLGFVKL

SEQ ID NO: 13 is a linker which corresponds to the following sequence: RSPQPQPKPQPKPEPEGSLQ.

SEQ ID NO: 7 is coded by the sequence in nucleotides SEQ ID NO: 14 which corresponds to the following sequence:

catgaccaggaaaccacgactcaagaccccggagtcctgctcccctgccc aaggggcctgcacaggttggatggcgggcaccccagggcatccgggcca taatggggcccaggccgtgatggcagagatggcaccctggtgagaagg gtgagaaaggagatccaggtcttattgtgcctaagggagacatcggtgaa accggagtacccggggctgaaggtccccgaggctttccgggaatccaagg caggaaaggagaacctggagaaggtttcgcagtgctcacccaaaaacaga agaagcagcactctgtcctgacctggttcccattaacgccacctccaagg atgactccgatgtgacagaggtgatggcaaccagctcttaggcgtgggag aggcctacaggcccaaggtatggtgtccgaatccaggatgctggagttt atctgctgtatagccaggtcctgtttcaagacgtgactttcaccatgggt caggtggtgtctcgagaaggccaaggaaggcaggagactctattccgatg tataagaagtatgccctcccacccggaccgggctacaacagctgctatag cgcaggtgtcttccatttacaccaaggggatattctgagtgtcataattc cccgggcaagggcgaaacttaacctctctccacatggaaccttcctgggg tttgtgaaactgtga SEQ ID NO: 8 is coded by the sequence in nucleotides SEQ ID NO: 15 which corresponds to the following sequence:

catgaccaggaaaccacgactcaagggcccggagtcctgcaccctgcc caaggggcctgcacaggttggatggcgggcatcccagggcatccgggc cataatggggcccaggccgtgatggcagagatggcaccctggtgaga agggtgagaaaggagatccaggtcttattggtcctaagggagacatcgg tgaaaccggagtacccggggctgaaggtccccgaggctttccgggaatc caattgcaggaaaggagaacctggagaaggtgcccactctgtcctgcac ctggttcccattaacgccacctccaaggatgactccgatgtgacagagg tgtagccaggtcctgtttcaagacgtgactacaccatggtccaggtggt gtctcgagaaggccaaggaaggcaggattactctattccgatgtataag aagtatgccctcccacccggaccgggcctacaacagctgctatagcgca ggtgtatccatttacaccaaggggatattctgagtgtcataattccccG ggcaagggcgaAacttaacctctctccacatggaaccttcctggggttt gtgaaactgtga SEQ ID NO: 9 is coded by the sequence in nucleotides SEQ ID NO: 16 which corresponds to the following sequence:

ATGGCTATCATCTACCTCATCCTCCTGTTCACCGCTGTGCGGGCCTCGA

CAAAACTCACACATGCCCACCGTGCTCAGCACCTGAACTCTTGGGGGGAC

CGTCAGTCTTCTTCTTCCCCCCAAAACCCAAGGACACCCTCATGATCTCC

CGGACCCCTGAGGTCACATGCGTGGTGGTGGACGTGAGCCACGAAGACCC

TGAGGTCAAGTTCAACTGGTACGTGGACGGCGTGGAGGTGCATAATGCCA

AGACAAAGCCGCGGGAGGAGCAGTACAACAGCACGTACCGTGTGGTCAGC

GTCCTCACCGTCCTGCACCAGGACTGGCTGAATGGCAAGGAGTACAAGTG

CAAGGTCTCCAACAAAGCCCTCCCAGCCCCCATCGAGAAAACCATCTCCT

AAGCCAAAGGGCAGCCCCGAGAACCACAGGTGTACACCCTGCCCCCATCC

CGGGATGAGCTGACCTAGAACCAGGTCAGCCTGACCTGCCTGGTCAAAGG

CTTCTATCCCAGCGACATCGCCGTGGAGTGGGAGAGCAATGGGCAGCCGG

AGAACAACTACAAGACCACGCCTCCCGTGTTGGACTCCGTCGGCTCCTTC

TTCCTCTACAGCAAGCTCACCGTGGACAAGAGCAGGTGGCAGCAGGGGTA

CGTCTTCTCATGCTCCGTGATGCATGAGGCTCTGCACAACCACTACACGC

AGAAGAGCCTCTCCCTGTCTCCGGGTAAAAGATCTCCGCAGCCGCAGCCG

ATACCGCAGCCGAAACCGGTACCGGTAGGATCCCTGCAGGCAGTGCTCAC

CCAAAAACAGAAGAAGCAGCACTCTGTCCTGCACCTGGTTCCCATTAACG

CCACCTCCAAGGATGACTCCGATGTGACAGAGGTGATGTGGCAACCAGCT

CTTAGGCGTGGGAGAGGCCTACAGGCCCAAGGATATGGTGTCCGAATCCA

GGATGCTGGAGTTTATCTGCTGTATAGCCAGGTCCTGTTTCAAGACGTGA

CTTTCACCATGGGTCAGGTGGTGTCTCGAGAAGGCCAAGGAAGGCAGGAG

ACTCTATTCCGATGTATAAGAAGTATGCCCTCCCACCCGGACCGCGCCTA

CAACAGCTGCTATAGCGCAGGTGTCTTCCATTTACACCAAGGGGATATTC

TGAGTGTCATAATTCCCCGGGCAAGGGCGAAACTTAACCTCTCTCCACAT

GGAACCTTCCTGGGGTTTGTGAAACTG

SEQ ID NO: 10 is coded by the sequence in nucleotides SEQ ID NO: 17 which corresponds to the following sequence:

ATGGCTATCATCTACCTCATCCTCCTGTTCACCGCTGTGCGGGCCTCGA

CAAAACTCACACATGCCCACCGTGCCCAGCACCTGAACTCCTGGGGGGAC

CGTCAGTCTTCCTCTTCCCCCCAAAACCCAAGGACACCCTCATGATCTCC

CGGACCCCTGAGGTCACATGCGTGGTGGTGGACGTGAGCCACGAAGACCC

TGAGGTCAAGTTCAACTGGTACGTGGACGGCGTGGAGGTGCATAATGCCA

AGACATAGCCGCGGGAGGAGCAGTACAACAGCACGTACCGTGTGGTCAGC

GTCCTCACCGTCCTGCACCAGGACTGGCTGAATGGCAAGGAGTACAAGTG

CAAGGTCTCCAACAAAGCCCTCCCAGCCCCCATCGAGAAAACCATCTCCA

AAGCCAAAGGGCAGCCCCGAGAACCACAGGTGTACACCCTGCCCCCATCC

CGGGATGAGCTGACCAAGAACCAGGTCAGCCTGACCTGCCTGGTCAAAGG

CTTCTATCCCAGCGACATCGCCGTGGAGTGGGAGAGCAATGGGCAGCCGG

AGAACAACTACAAGACCACGCCTCCCGTGTTGGACTCCGACGGCTCCTTC

TTCCTCTACAGCAAGCTCACCGTGGACAAGAGCAGGTGGCAGCAGGGGAA

```
CGTCTTCTCATGCTCCGTGATGOATGAGGCTCTGCACAACCACTACACGC

AGAAGAGCCTCTCCCTGTCTCCGGGTAAAAGATCTCCGCAGCCGCAGCCG

AAACCGCAGCCGAAACCGGAACCGGAAGGATCCCTGCAGCACTCTGTCCT

GCACCTGGTTCCCATTAACGCCACCTCCAAGGATGACTCCGATGTGACAG

AGGTGATGTGGCAACCAGCTCTTAGGCGTGGGAGAGGCCTACAGGCCCAA

GGATATGGTGTCCGAATCCAGGATGCTGGAGTTTATCTGCTGTATAGCCA

GGTCCTGTTTCAAGACGTGACTTTCACCATGGGTCAGGTGGTGTCTCGAG

AAGGCCAAGGAAGGCAGGAGACTCTATTCCGATGTATAAGAAGTATGCCC

TCCCACCCGGACCGGGCCTACAACAGCTGCTATAGCGCAGGTGTCTTCCA

TTTACACCAAGGGGATATTCTGAGTGTCATAATTCCCCGGGCAAGGGCGA

AACTTAACCTCTCTCCACATGGAACCTTCCTGGGGTTTGTGAAACTG
```

In a third embodiment, the present invention also relates to a composition comprising an active substance which comprises or consists in:
- a protein comprising the sequence SEQ ID NO: 1, representing the APRIL protein,
- or any derived protein, which is derived from protein of sequence SEQ ID NO: 1 by substitution, removal or addition of one or more amino-acids, provided it allows the binding of the said derived protein to an astrocyte and/or to CSPG,
- or any homologous protein, the sequence of which has a percentage of identity of at least approximately 70%, and in particular 85% with said sequence SEQ ID NO: 1, provided it allows the binding of the said homologous protein to an astrocyte and/or to CSPG,
- or any fragment of the protein of sequence SEQ ID NO: 1, provided it allows the binding of the said fragment to an astrocyte and/or to CSPG, for its use as a drug.

In another embodiment, the present invention also relates to a composition comprising an active substance comprises or consists in:
- a protein comprising the sequence SEQ ID NO: 1, representing the APRIL protein,
- or any derived protein, which is derived from protein of sequence SEQ ID NO: 1 by substitution, removal or addition of one or more amino-acids, provided it allows the binding of the said derived protein to an astrocyte,
- or any homologous protein, the sequence of which has a percentage of identity of at least approximately 70%, and in particular 85% with said sequence SEQ ID NO: 1, provided it allows the binding of the said homologous protein to an astrocyte,
- or any fragment of the protein of sequence SEQ ID NO: 1, provided it allows the binding of the said fragment to an astrocyte, for its use for the manufacture of a drug for the prevention or the treatment of an autoimmune disorder, or for its use for the prevention or the treatment of an autoimmune disorder.

In another embodiment, the present invention also relates to a composition comprising an active substance comprises or consists in:
- a protein comprising the sequence SEQ ID NO: 1, representing the APRIL protein,
- or any derived protein, which is derived from protein of sequence SEQ ID NO: 1 by substitution, removal or addition of one or more amino-acids, provided it allows the binding of the said derived protein to CSPG,
- or any homologous protein, the sequence of which has a percentage of identity of at least approximately 70%, and in particular 85% with said sequence SEQ ID NO: 1, provided it allows the binding of the said homologous protein to CSPG,
- or any fragment of the protein of sequence SEQ ID NO: 1, provided it allows the binding of the said fragment to CSPG, for its use for the manufacture of a drug for the prevention or the treatment of an autoimmune disorder, or for its use for the prevention or the treatment of an autoimmune disorder.

In another embodiment, the present invention relates to a composition comprising an active substance which comprises or consists in:
- a protein comprising the sequence SEQ ID NO: 1, representing the APRIL protein,
- or any derived protein, which is derived from protein of sequence SEQ ID NO: 1 by substitution, removal or addition of one or more amino-acids, provided it allows the binding of the said derived protein to an astrocyte and/or to CSPG,
- or any homologous protein, the sequence of which has a percentage of identity of at least approximately 70%, and in particular 85% with said sequence SEQ ID NO: 1, provided it allows the binding of the said homologous protein to an astrocyte and/or to CSPG,
- or any fragment of the protein of sequence SEQ ID NO: 1, provided it allows the binding of the said fragment to an astrocyte and/or to CSPG, for its use for the prevention or the treatment of a neurodegenerative disease.

In another embodiment, the invention relates to a composition comprising an active substance comprises or consists in:
- a protein comprising the sequence SEQ ID NO: 2, representing the APRIL protein,
- or any derived protein, which is derived from protein of sequence SEQ ID NO: 2 by substitution, removal or addition of one or more amino-acids, provided it allows the binding of the said derived protein to an astrocyte and/or to CSPG,
- or any homologous protein, the sequence of which has a percentage of identity of at least approximately 70%, and in particular 85% with said sequence SEQ ID NO: 2, provided it allows the binding of the said homologous protein to an astrocyte and/or to CSPG,
- or any fragment of the protein of sequence SEQ ID NO: 2, provided it allows the binding of the said fragment to an astrocyte and/or to CSPG, for its use as a drug.

In another embodiment, the invention relates to a composition comprising an active substance comprises or consists in:
- a protein comprising the sequence SEQ ID NO: 2, representing the APRIL protein,
- or any derived protein, which is derived from protein of sequence SEQ ID NO: 2 by substitution, removal or addition of one or more amino-acids, provided it allows the binding of the said derived protein to an astrocyte,
- or any homologous protein, the sequence of which has a percentage of identity of at least approximately 70%, and in particular 85% with said sequence SEQ ID NO: 2, provided it allows the binding of the said homologous protein to an astrocyte, or any fragment of the protein of sequence SEQ ID NO: 2, provided it allows the binding of the said fragment to an astrocyte, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:
- a protein comprising the sequence SEQ ID NO: 2, representing the APRIL protein,
- or any derived protein, which is derived from protein of sequence SEQ ID NO: 2 by substitution, removal or addition of one or more amino-acids, provided it allows the binding of the said derived protein to CSPG,
- or any homologous protein, the sequence of which has a percentage of identity of at least approximately 70%, and in particular 85% with said sequence SEQ ID NO: 2, provided it allows the binding of the said homologous protein to CSPG,
- or any fragment of the protein of sequence SEQ ID NO: 2, provided it allows the binding of the said fragment to CSPG, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:
- a protein comprising the sequence SEQ ID NO: 2, representing the APRIL protein,
- or any derived protein, which is derived from protein of sequence SEQ ID NO: 2 by substitution, removal or addition of one or more amino-acids, provided it allows the binding of the said derived protein to an astrocyte and/or to CSPG,
- or any homologous protein, the sequence of which has a percentage of identity of at least approximately 70%, and in particular 85% with said sequence SEQ ID NO: 2, provided it allows the binding of the said homologous protein to an astrocyte and/or to CSPG,
- or any fragment of the protein of sequence SEQ ID NO: 2, provided it allows the binding of the said fragment to an astrocyte and/or to CSPG, for its use for the prevention or the treatment of a neurodegenerative disease.

In another embodiment, the invention relates to a composition comprising an active substance comprises or consists in:
- a protein comprising the sequence SEQ ID NO: 3, representing the APRIL protein,
- or any derived protein, which is derived from protein of sequence SEQ ID NO: 3 by substitution, removal or addition of one or more amino-acids, provided it allows the binding of the said derived protein to an astrocyte and/or to CSPG,
- or any homologous protein, the sequence of which has a percentage of identity of at least approximately 70%, and in particular 85% with said sequence SEQ ID NO: 3, provided it allows the binding of the said homologous protein to an astrocyte and/or to CSPG,
- or any fragment of the protein of sequence SEQ ID NO: 3, provided it allows the binding of the said fragment to an astrocyte and/or to CSPG, for its use as a drug.

In another embodiment, the invention relates to a composition comprising an active substance comprises or consists in:
- a protein comprising the sequence SEQ ID NO: 3, representing the APRIL protein,
- or any derived protein, which is derived from protein of sequence SEQ ID NO: 3 by substitution, removal or addition of one or more amino-acids, provided it allows the binding of the said derived protein to an astrocyte,
- or any homologous protein, the sequence of which has a percentage of identity of at least approximately 70%, and in particular 85% with said sequence SEQ ID NO: 3, provided it allows the binding of the said homologous protein to an astrocyte,
- or any fragment of the protein of sequence SEQ ID NO: 3, provided it allows the binding of the said fragment to an astrocyte, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:
- a protein comprising the sequence SEQ ID NO: 3, representing the APRIL protein,
- or any derived protein, which is derived from protein of sequence SEQ ID NO: 3 by substitution, removal or addition of one or more amino-acids, provided it allows the binding of the said derived protein to CSPG,
- or any homologous protein, the sequence of which has a percentage of identity of at least approximately 70%, and in particular 85% with said sequence SEQ ID NO: 3, provided it allows the binding of the said homologous protein to CSPG,
- or any fragment of the protein of sequence SEQ ID NO: 3, provided it allows the binding of the said fragment to CSPG, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:
- a protein comprising the sequence SEQ ID NO: 3, representing the APRIL protein,
- or any derived protein, which is derived from protein of sequence SEQ ID NO: 3 by substitution, removal or addition of one or more amino-acids, provided it allows the binding of the said derived protein to an astrocyte and/or to CSPG,
- or any homologous protein, the sequence of which has a percentage of identity of at least approximately 70%, and in particular 85% with said sequence SEQ ID NO: 3, provided it allows the binding of the said homologous protein to an astrocyte and/or to CSPG,
- or any fragment of the protein of sequence SEQ ID NO: 3, provided it allows the binding of the said fragment to an astrocyte and/or to CSPG, for its use for the prevention or the treatment of a neurodegenerative disease.

In another embodiment, the invention relates to a composition comprising an active substance comprises or consists in:
- a nucleotidic sequence coding for a protein comprising the SEQ ID NO: 1 or a nucleotidic sequence of SEQ ID NO: 4, coding for a protein having the sequence SEQ ID NO: 1, or any derived nucleotidic sequence, by degeneration of code genetic, of sequence SEQ ID NO: 4, or any derived nucleotidic sequence, by substitution, suppression or addition of one or more nucleotides, sequence SEQ ID NO: 4, or any homologous nucleotidic sequence having a percentage of identity of at least approximately 70%, with sequence SEQ ID NO: 4, or any fragment of nucleotidic sequence SEQ ID NO: 4 or of the above defined nucleotidic sequences, the aforementioned fragment preferably making up of at least approximately 20 contiguous nucleotides in the aforementioned sequence, for its use as a drug.

In another embodiment, the invention relates to a composition comprising an active substance comprises or consists in:

a nucleotidic sequence coding for a protein comprising the SEQ ID NO: 1 or a nucleotidic sequence of SEQ ID NO: 4, coding for a protein having the sequence SEQ ID NO: 1, or any derived nucleotidic sequence, by degeneration of code genetic, of sequence SEQ ID NO: 4, or any derived nucleotidic sequence, by substitution, suppression or addition of one or more nucleotides, sequence SEQ ID NO: 4, or any homologous nucleotidic sequence having a percentage of identity of at least approximately 70%, with sequence SEQ ID NO: 4.

or any fragment of nucleotidic sequence SEQ ID NO: 4 or of the above defined nucleotidic sequences, the aforementioned fragment preferably making up of at least approximately 20 contiguous nucleotides in the aforementioned sequence, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:

a nucleotidic sequence coding for a protein comprising the SEQ ID NO: 1 or a nucleotidic sequence of SEQ ID NO: 4, coding for a protein having the sequence SEQ ID NO: 1, or any derived nucleotidic sequence, by degeneration of code genetic, of sequence SEQ ID NO: 4, or any derived nucleotidic sequence, by substitution, suppression or addition of one or more nucleotides, sequence SEQ ID NO: 4, or any homologous nucleotidic sequence having a percentage of identity of at least approximately 70%, with sequence SEQ ID NO: 4, or any fragment of nucleotidic sequence SEQ ID NO: 4 or of the above defined nucleotidic sequences, the aforementioned fragment preferably making up of at least approximately 20 contiguous nucleotides in the aforementioned sequence, for its use for the prevention or the treatment of a neurodegenerative disease.

In another embodiment, the invention relates to a composition comprising an active substance comprises or consists in:

a nucleotidic sequence coding for a protein comprising the SEQ ID NO: 2 or a nucleotidic sequence of SEQ ID NO: 5, coding for a protein having the sequence SEQ ID NO: 2, or any derived nucleotidic sequence, by degeneration of code genetic, of sequence SEQ ID NO: 5, or any derived nucleotidic sequence, by substitution, suppression or addition of one or more nucleotides, sequence SEQ ID NO: 5, or any homologous nucleotidic sequence having a percentage of identity of at least approximately 70%, with sequence SEQ ID NO: 5, or any fragment of nucleotidic sequence SEQ ID NO: 5 or of the above defined nucleotidic sequences, the aforementioned fragment preferably making up of at least approximately 20 contiguous nucleotides in the aforementioned sequence, for its use as a drug.

In another embodiment, the invention relates to a composition comprising an active substance comprises or consists in:

a nucleotidic sequence coding for a protein comprising the SEQ ID NO: 2 or a nucleotidic sequence of SEQ ID NO: 5, coding for a protein having the sequence SEQ ID NO: 2, or any derived nucleotidic sequence, by degeneration of code genetic, of sequence SEQ ID NO: 5, or any derived nucleotidic sequence, by substitution, suppression or addition of one or more nucleotides, sequence SEQ ID NO: 5, or any homologous nucleotidic sequence having a percentage of identity of at least approximately 70%, with sequence SEQ ID NO: 5.

or any fragment of nucleotidic sequence SEQ ID NO: 5 or of the above defined nucleotidic sequences, the aforementioned fragment preferably making up of at least approximately 20 contiguous nucleotides in the aforementioned sequence, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:

a nucleotidic sequence coding for a protein comprising the SEQ ID NO: 2 or a nucleotidic sequence of SEQ ID NO: 5, coding for a protein having the sequence SEQ ID NO: 2, or any derived nucleotidic sequence, by degeneration of code genetic, of sequence SEQ ID NO: 5, or any derived nucleotidic sequence, by substitution, suppression or addition of one or more nucleotides, sequence SEQ ID NO: 5, or any homologous nucleotidic sequence having a percentage of identity of at least approximately 70%, with sequence SEQ ID NO: 5, or any fragment of nucleotidic sequence SEQ ID NO: 5 or of the above defined nucleotidic sequences, the aforementioned fragment preferably making up of at least approximately 20 contiguous nucleotides in the aforementioned sequence, for its use for the prevention or the treatment of a neurodegenerative disease.

In another embodiment, the invention relates to a composition comprising an active substance comprises or consists in:

a nucleotidic sequence coding for a protein comprising the SEQ ID NO: 3 or a nucleotidic sequence of SEQ ID NO: 6, coding for a protein having the sequence SEQ ID NO: 3, or any derived nucleotidic sequence, by degeneration of code genetic, of sequence SEQ ID NO: 6, or any derived nucleotidic sequence, by substitution, suppression or addition of one or more nucleotides, sequence SEQ ID NO: 6, or any homologous nucleotidic sequence having a percentage of identity of at least approximately 70%, with sequence SEQ ID NO: 6.

or any fragment of nucleotidic sequence SEQ ID NO: 6 or of the above defined nucleotidic sequences, the aforementioned fragment preferably making up of at least approximately 20 contiguous nucleotides in the aforementioned sequence, for its use as a drug.

In another embodiment, the invention relates to a composition comprising an active substance comprises or consists in:

a nucleotidic sequence coding for a protein comprising the SEQ ID NO: 3 or a nucleotidic sequence of SEQ ID NO: 6, coding for a protein having the sequence SEQ ID NO: 3, or any derived nucleotidic sequence, by degeneration of code genetic, of sequence SEQ ID NO: 6, or any derived nucleotidic sequence, by substitution, suppression or addition of one or more nucleotides, sequence SEQ ID NO: 6, or any homologous nucleotidic sequence having a percentage of identity of at least approximately 70%, with sequence SEQ ID NO: 6, or any fragment of nucleotidic sequence SEQ ID NO: 6 or of the above defined nucleotidic sequences, the aforementioned fragment preferably making up of at least approximately 20 contiguous nucleotides in the aforementioned sequence, for its use for the manufacture of a drug for the prevention or the treatment of an autoimmune disorder, or for its use for the prevention or the treatment of an autoimmune disorder.

In another embodiment, the invention relates to a composition comprising an active substance comprises or consists in:

a nucleotidic sequence coding for a protein comprising the SEQ ID NO: 3 or a nucleotidic sequence of SEQ ID NO: 6, coding for a protein having the sequence SEQ ID NO: 3, or any derived nucleotidic sequence, by degeneration of code genetic, of sequence SEQ ID NO: 6, or any derived nucleotidic sequence, by substitution, suppression or addition of one or more nucleotides, sequence SEQ ID NO: 6, or any homologous nucleotidic sequence having a percentage of identity of at least approximately 70%, with sequence SEQ ID NO: 6, or any fragment of nucleotidic sequence SEQ ID NO: 6 or of the above defined nucleotidic sequences, the aforementioned fragment preferably making up of at least approximately 20 contiguous nucleotides in the aforementioned sequence, for its use for the prevention or the treatment of a neurodegenerative disease.

In another embodiment, the invention relates to a composition wherein the active substance comprises or consists in a vector in particular, plasmid, cosmid, phage or DNA of virus, containing a sequence chosen among SEQ ID NO: 4 or SEQ ID NO: 5 or SEQ ID NO: 6, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the protein has one of the sequences SEQ ID NO: 1 or SEQ ID NO: 2 or SEQ ID NO: 3, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the protein is a chimeric protein constituted by an oligomer of the protein of one of the sequences SEQ ID NO: 1 or SEQ ID NO: 2 or SEQ ID NO: 3, or a derived protein, or a homologous protein or a fragment of one of the sequences SEQ ID NO: 1 or SEQ ID NO: 2 or SEQ ID NO: 3, each protein or fragment being linked to the other by a constant region of an immunoglobulin, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the protein is a chimeric protein constituted by an oligomer of the protein of one of the sequences SEQ ID NO: 1 or SEQ ID NO: 2 or SEQ ID NO: 3, or a derived protein, or a homologous protein or a fragment of one of the sequences SEQ ID NO: 1 or SEQ ID NO: 2 or SEQ ID NO: 3, each protein or fragment being linked to the headless region of a ACRP30 protein, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the active substance forms a complex with an astrocyte and/or CSPG, for its use as a drug, or for its use for the manufacture of a drug for the prevention or the treatment of an autoimmune disorder, or for its use for the prevention or the treatment of an autoimmune disorder or a neurodegenerative disease.

The complex used as a drug or the complex used for the manufacture of a drug for the prevention or the treatment of an autoimmune disorder or the complex used for the prevention or the treatment of an autoimmune disorder or a neurodegenerative disease can be formed by one active substance and one astrocyte and/or CSPG or several active substances and one astrocyte and/or CSPG.

For example, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the other by a constant region of an immunoglobulin.

The complex used as a drug or the complex used for the manufacture of a drug for the prevention or the treatment of an autoimmune disorder or the complex used for the prevention or the treatment of an autoimmune disorder or a neurodegenerative disease can also be formed between one astrocyte and/or CSPG and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the headless region of a ACRP30 protein.

The complex used as a drug or the complex used for the manufacture of a drug for the prevention or the treatment of an autoimmune disorder or the complex used for the prevention or the treatment of an autoimmune disorder or a neurodegenerative disease can also be formed between one astrocyte and/or CSPG and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the other by a constant region of an immunoglobulin and one or several chimeric proteins constituted by an oligomer of the protein of sequence SEQ ID NO: 1 or SEQ ID NO: 2 or SEQ ID NO: 3, or a derived protein, or a homologous protein or a fragment of the sequence SEQ ID NO: 1 or SEQ ID NO: 2 or SEQ ID NO: 3, each protein or fragment being linked to the headless region of a ACRP30 protein.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $A_{88}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $A_{88}$ and one or several chimeric proteins MEGA-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins Fc-APRIL $A_{88}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins Fc-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins Fc-APRIL $A_{88}$ and one or several chimeric proteins Fc-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL As and one or several chimeric proteins Fc-APRIL $A_{88}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $A_{88}$ and one or several chimeric proteins Fc-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $H_{98}$ and one or several chimeric proteins Fc-APRIL $A_{88}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $H_{98}$ and one or several chimeric proteins Fc-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins Fc-APRIL $A_{88}$ and one or several chimeric proteins Fc-APRIL $H_{98}$ and one or several MEGA-APRIL $A_{88}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins Fc-APRIL $A_{88}$ and one or several chimeric proteins Fc-APRIL $H_{98}$ and one or several MEGA-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $A_{88}$ and one or several chimeric proteins MEGA-APRIL $H_{98}$ and one or several chimeric proteins Fc-APRIL $A_{88}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $A_{88}$ and one or several chimeric proteins MEGA-APRIL $H_{98}$ and one or several chimeric proteins Fc-APRIL $H_{98}$.

In a particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed between one astrocyte and/or CSPG and one or several chimeric proteins MEGA-APRIL $A_{88}$ and one or several chimeric proteins MEGA-APRIL $H_{98}$ and one or several chimeric proteins Fc-APRIL $A_{88}$ and one or several chimeric proteins Fc-APRIL $H_{98}$.

In another particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed by one active substance as defined above and one neuron or several active substances as defined above and one neuron.

In another particular embodiment, the complex used as a drug or the complex used for the manufacture of a drug for the prevention or the treatment of an autoimmune disorder or the complex used for the prevention or the treatment of an autoimmune disorder or a neurodegenerative disease can be formed by one active substance as defined above and one oligodendrocyte or several active substances as defined above and one oligodendrocyte.

In another embodiment, the invention relates to a composition wherein the protein of one of the sequences SEQ ID NO: 1 or SEQ ID NO: 2 or SEQ ID NO: 3 is the active substance which forms a complex with an astrocyte and/or CSPG, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the chimeric protein constituted by an oligomer of the protein of one of the sequences SEQ ID NO: 1 or SEQ ID NO: 2 or SEQ ID NO: 3, or a derived protein, or a homologous protein or a fragment of one of the sequences SEQ ID NO: 1 or SEQ ID NO: 2 or SEQ ID NO: 3, each protein or fragment being linked to the other by a constant region of an immunoglobulin, is the active substance which forms a complex with an astrocyte and/or CSPG, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the chimeric protein constituted by an oligomer of the protein of one of the sequences SEQ ID NO: 1 or SEQ ID NO: 2 or SEQ ID NO: 3, or a derived protein, or a homologous protein or a fragment of one of the sequences SEQ ID NO: 1 or SEQ ID NO: 2 or SEQ ID NO: 3, each protein or fragment being linked to the headless region of a ACRP30 protein, is the active substance which forms a complex with an astrocyte and/or CSPG, for its use as a drug, or for the its use for the manufacture of a drug for the prevention or the treatment of an autoimmune disorder, or for its use for the prevention or the treatment of an autoimmune disorder or a neurodegenerative disease.

In another embodiment, the invention relates to a composition wherein a chimeric protein comprising or consisting in SEQ ID NO: 7 or SEQ ID NO: 8 or SEQ ID NO: 9 or SEQ ID NO: 10 is the active substance which forms a complex with an astrocyte and/or CSPG, for its use as a drug, or for its use for the manufacture of a drug for the prevention or the treatment of an autoimmune disorder, or for its use for the prevention or the treatment of an autoimmune disorder or a neurodegenerative disease.

In another embodiment, the invention relates to a composition wherein the active substance is formulated for administration in a range of doses from about 0.1 mg/kg to about 20 mg/kg, for its use as a drug, or for its use for the manufacture of a drug for the prevention or the treatment of an autoimmune disorder, or for its use for the prevention or the treatment of an autoimmune disorder or a neurodegenerative disease.

The expression "doses from about 0.1 mg/kg to about 20 mg/kg" means for example 0.1 mg/kg; 0.2 mg/kg; 0.3 mg/kg; 0.4 mg/kg; 0.4 mg/kg; 0.5 mg/kg; 0.6 mg/kg; 0.7 mg/kg; 0.8 mg/kg; 0.9 mg/kg; 1.0 mg/kg; 2.0 mg/kg; 3.0 mg/kg; 4.0 mg/kg; 5.0 mg/kg; 6.0 mg/kg; 7.0 mg/kg; 8.0 mg/kg; 9.0 mg/kg; 10.0 mg/kg; 11.0 mg/kg; 12.0 mg/kg; 13.0 mg/kg; 14.0 mg/kg; 15.0 mg/kg; 16.0 mg/kg; 17.0 mg/kg; 18.0 mg/kg; 19.0 mg/kg; 20.0 mg/kg.

In another embodiment, the invention relates to a composition wherein the autoimmune disorder is a neurodegenerative disease.

In another embodiment, the invention relates to a composition wherein the autoimmune disorder is selected from: multiple sclerosis, autoimmune encephalitis, neuromyelitis optica (NMO), neurolupus, neurobehcet, neurosjogren, neurosarcoidosis, acute disseminated encephalomyelitis (ADEM), clinically isolated syndrome, multifocal motor neuropathy (MMN), anti-MAG neuropathy, neuropathy associated with paraptoteinemia, chronic inflammatory demyelinating polyneuropathy (CIDP), Guillain-Barré syndrome, for its use for the manufacture of a drug for the prevention or the treatment of an autoimmune disorder, or for its use for the prevention or the treatment of an autoimmune disorder.

In a particular embodiment, the multiple sclerosis is a relapsing remitting multiple sclerosis (RRMS) or a primary progressive multiple sclerosis (PPMS) or a secondary progressive multiple sclerosis (SPMS) or a progressive relapsing multiple sclerosis (PRMS).

In another embodiment, the invention relates to a composition for its use for the manufacture of a drug for the prevention or the treatment of the multiple sclerosis, or for its use for the prevention or the treatment of the multiple sclerosis.

In another embodiment, the invention relates to a composition wherein the neurodegenerative disease is selected from: Alzheimer disease, Parkinson Disease, Schizophrenia and Sclerosis Lateral Amyotrophic.

In another embodiment, the invention relates to a composition for its use for the prevention or the treatment of Alzheimer disease, Parkinson Disease, Schizophrenia and Sclerosis Lateral Amyotrophic.

The present invention is illustrated by the following Figures and Examples, which do not limit the scope of the invention.

Single and merge stainings are shown. Nuclear DAPI staining has been added to the merge stainings.

Figure 4:
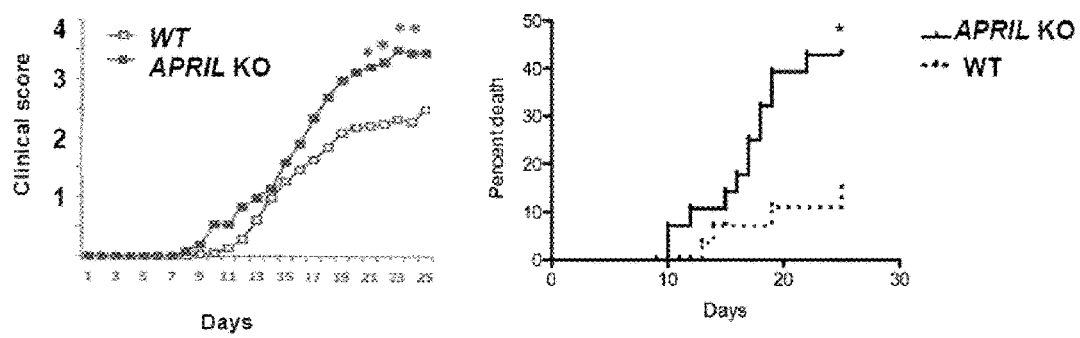

FIG. 4 represents experimental autoimmune encephalitis (EAE) induced by $MOG_{35-55}$ peptide immunization in wild-type mice (WT) or mice genetically deficient in APRIL (APRIL KO (knock-out) C57Bl/6 mice).

The clinical score (left panel) and death induced by EAE pathologies (right panel) are shown.

Abcissa represents the days after vaccination with the MOG peptide, and the ordinate axis represents the clinical score of the two mice groups.

Figure 5:
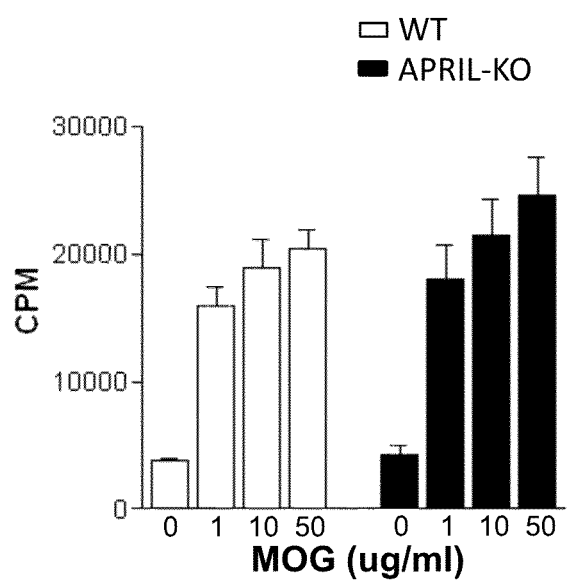

FIG. 5 represents the results of immunological responses between the two mice groups induced against the $MOG_{35-55}$ peptide used for animal priming (splenic T-cell proliferation).

The two mice groups are wild-type mice (WT) and mice genetically deficient in APRIL (APRIL KO (knock-out) C57Bl/6 mice), in which experimental autoimmune encephalitis (EAE) is induced by $MOG_{35-55}$ peptide immunization.

Abcissa represents the concentration of MOG peptide (ug/ml) (or µg/ml) and the ordinate axis shows incorporation of tritiated thymidine monitored by count per minute (CPM) for the two mice groups.

Figure 6:
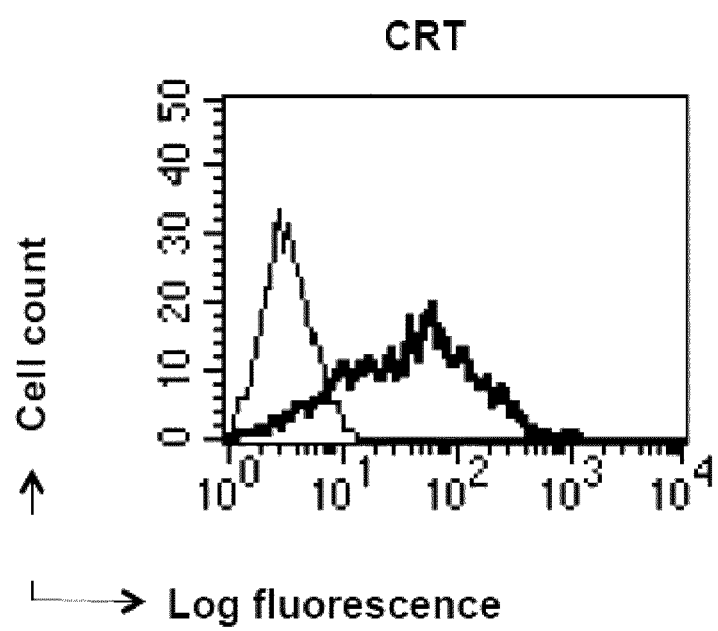

FIG. 6 represents CRT astrocytes immunostained with Fc-control (thin lines) and Fc-APRIL (bold lines), and analyzed by flow cytometry. Overlayed histogram plots are shown.

Figure 7A:
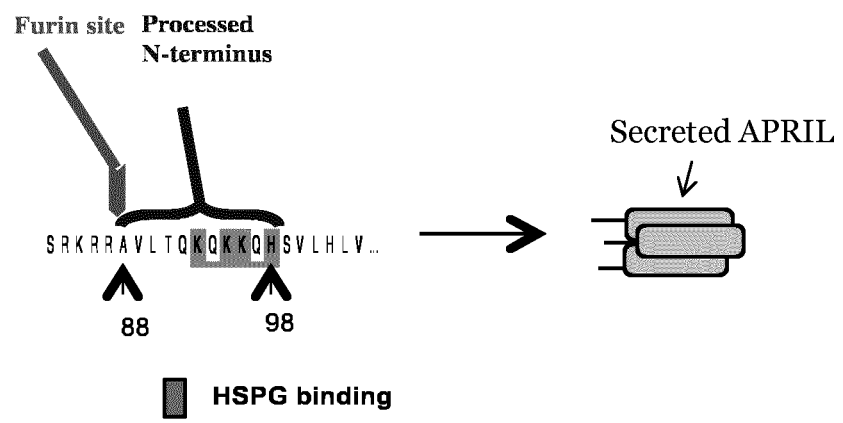

FIG. 7A represents a recombinant APRIL with indication of a furin site, a processed N-terminus and a HSPG binding domain (SEQ ID NO: 2).

FIG. 7B represents a recombinant APRIL with and without the HSPG binding Domain. Soluble recombinant APRIL forms starting at alanine 88 (A88) or histidine 98 (H98) have been generated. APRIL A88 (SEQ ID NO: 2) possesses the HSPG binding domain, APRIL H98 (SEQ ID NO: 1) 4e does not possess the HSPG binding domain.

The term valency means the maximal number of bonds that can be formed with an APRIL receptor.

Figure 8A:
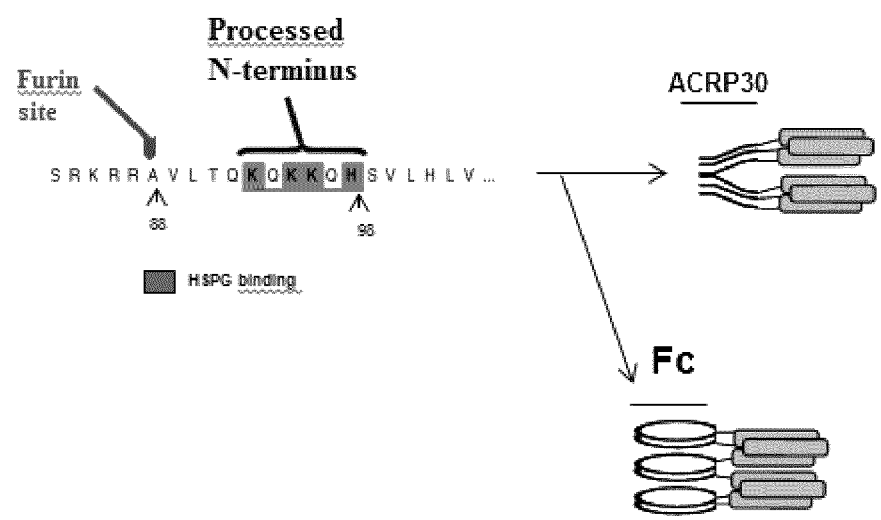

FIG. 8A represents a recombinant APRIL, with indication of a furin site, a processed N-terminus and a HSPG binding domain (SEQ ID NO: 2).

A schematic representation of an oligomer with the adipocyte complement-related protein of 30 kDa (ACRP30) (SEQ ID NO: 11) and a human Fc fragment (SEQ ID NO: 12) is also represented.

FIG. 8B represents soluble recombinant APRIL forms starting at alanine 88 (A88) and histidine 98 (H98), with and without the HSPG binding domain, respectively, oligomerized by fusion with the adipocyte complement-related protein of 30 kDa (ACRP30), respectively as Mega-APRIL $A_{88}$ (SEQ ID NO: 7) and Mega-APRIL $H_{98}$ (SEQ ID NO: 8), or a human Fc region, respectively as Fc-APRIL $A_{88}$ (SEQ ID NO: 9) and Fc-APRIL $A_{98}$ (SEQ ID NO: 10)

Figure 9:
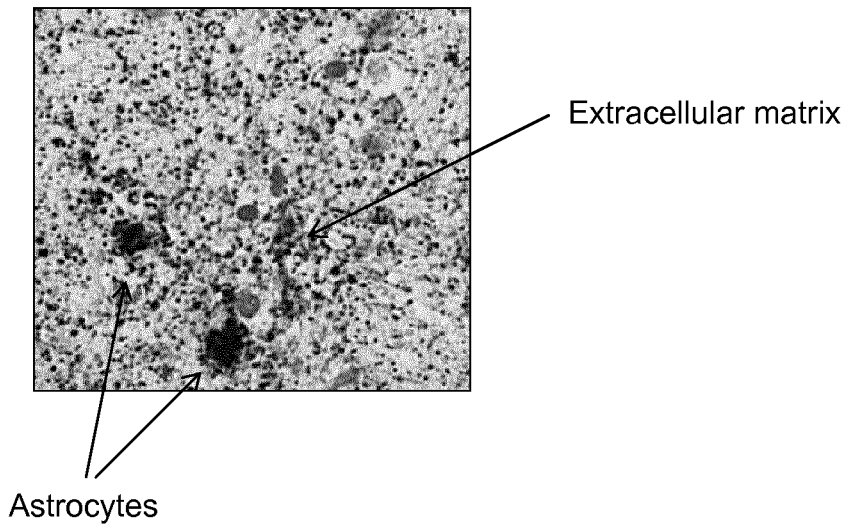

FIG. 9 represents a biopsy from a Multiple Sclerosis patient immunostained with Aprily-8. The binding to the astrocytes and the Extracellular Matrix is shown.

Figure 10:
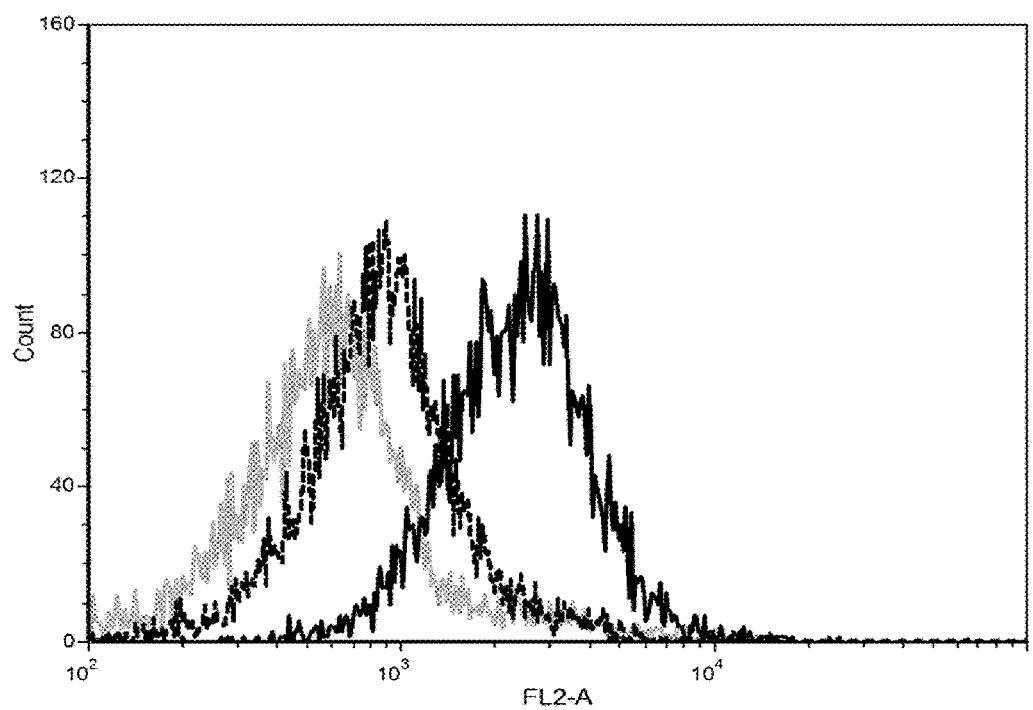

FIG. 10 represents CRT astrocytes immunostained with medium and APRIL in the presence or absence of inhibitory CSPG and analyzed by flow cytometry.

Abcissa represents the fluorescence intensity and the ordinate axis shows the number of cells.

The black line corresponds to the results of APRIL in absence of inhibitory CSPG, the black dashed line corresponds to the results of APRIL pre-incubated with CSPG, and the grey line corresponds to the control.

Figure 11:
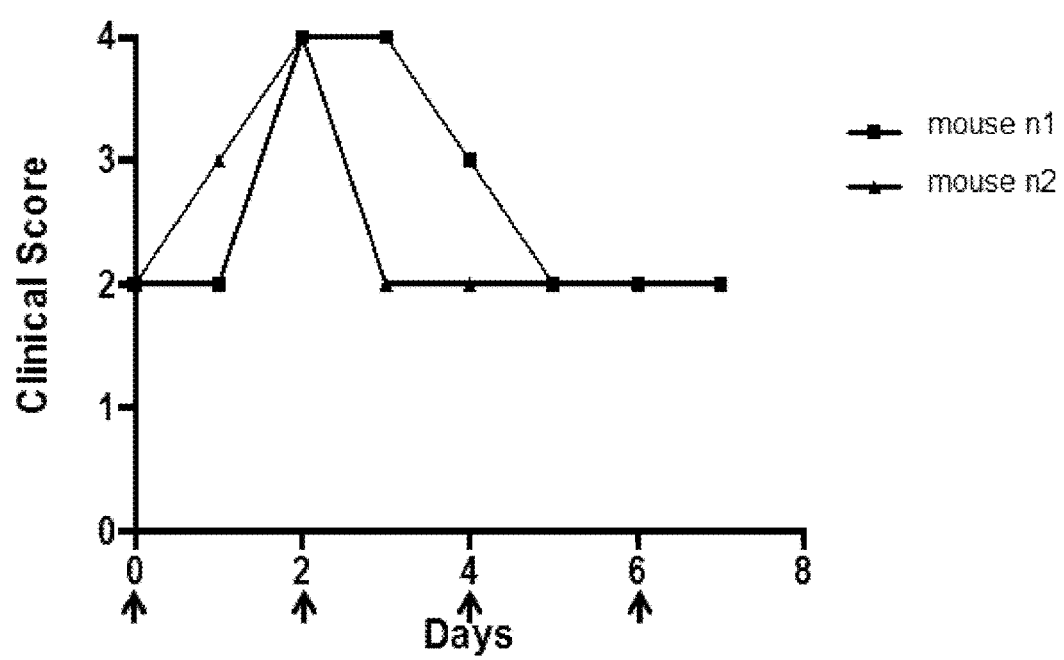

FIG. 11 represents the treatment by intravenous injection of APRIL of two mice with experimental autoimmune encephalitis.

Abcissa represents the day after the first APRIL injection and the ordinate axis represents the clinical score. Arrows indicate time of APRIL injections (0, 2, 4 and 6).

EXAMPLES

The following examples have been carried out according to the experimental procedures hereafter described.

Example 1: APRIL Expression in Multiple Sclerosis (MS) Patient Lesions—Human Studies The first tissue-reactive antibodies against human APRIL have been generated, as explained in Schwaller et al., *Blood*, vol 109, pp 331-337, 2007.

Figure 1:
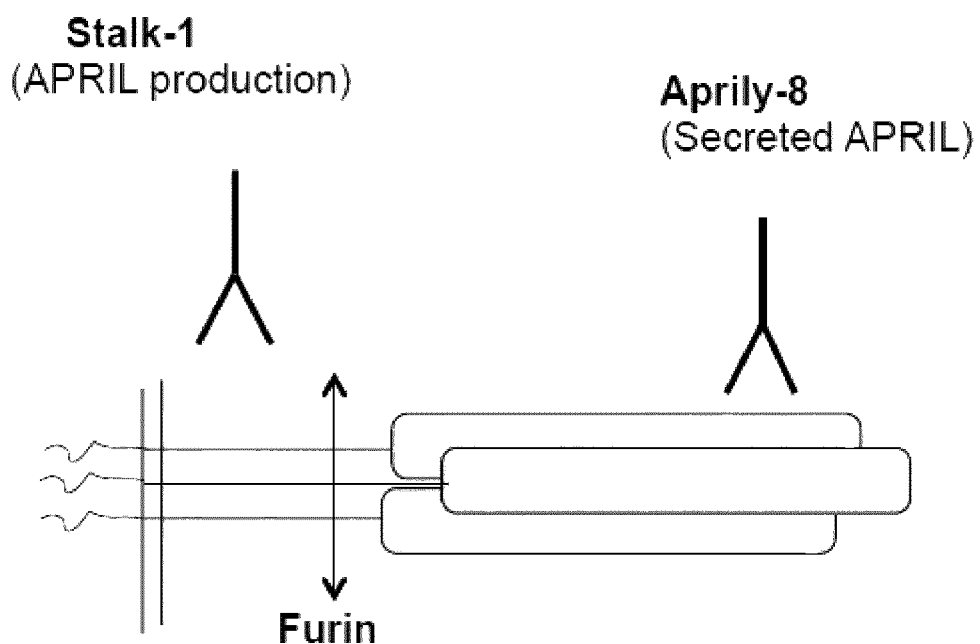
FIG. 1 represents a home-made tissue reactive anti-human APRIL. Furin cleavage site and reactivity of the tissue-reactive antibodies are indicated. One antibody, Aprily-8, reacts with the secreted product and another one, Stalk-1, reacts with the APRIL part remaining anchored at the membrane of producing cells after furin processing.

APRIL is a transmembrane protein undergoing cleavage by furin proteases in order to be secreted[18]. Antibodies which link to the two parts of the protein after cleavage are known. Indeed, one antibody, Aprily-8, reacts with the secreted product and another one, Stalk-1, reacts with the APRIL part remaining anchored at the membrane of producing cells after furin processing (see FIG. 1). Enzo Life Sciences distributes these antibodies.

There is no full-length product detected by this antibody pair in tissues[9], probably because of a fast processing after translation, so that Aprily-8 detects the localisation of secreted APRIL only and does not react with APRIL-producing cells.

1. Immunohistochemlistry (Stalk-1/Aprily-8)
Material & Methods

Serial sections form biopsies of the indicated patients were fixed, paraffin-embedded and subjected to immunostaining with Stalk-1 (5 µg/ml, rabbit polyclonal antibody recognizing cells producing APRIL) and Aprily-8 (2 µg/ml, mouse monoclonal antibody recognizing the secreted form of APRIL).

Indicated patients are patients with Multiple Sclerosis (upper panel) and patients with Parkinson disease (bottom panel).

Tissues were washed, and incubated with a biotin-conjugated rabbit and mouse Ig antiserum, respectively.

Tissues were washed, and incubated with horse raddish peroxidase (HRP)-conjugated streptavidin.

Tissue were washed and incubated with the HRP substrate amino ethyl courmarin. Light microscopy was analyzed with an Axiocam microscope (Carl Zeiss).

Pictures from a relevant case of an inflammatory (multiple sclerosis, MS) and a non-inflammatory (Parkinson disease) neurodegenerative disease are shown.
Results A perilesional production of APRIL and a lesional retention of the secreted product have been observed in multiple sclerosis (FIG. 2, upper panel).

Figure 2:
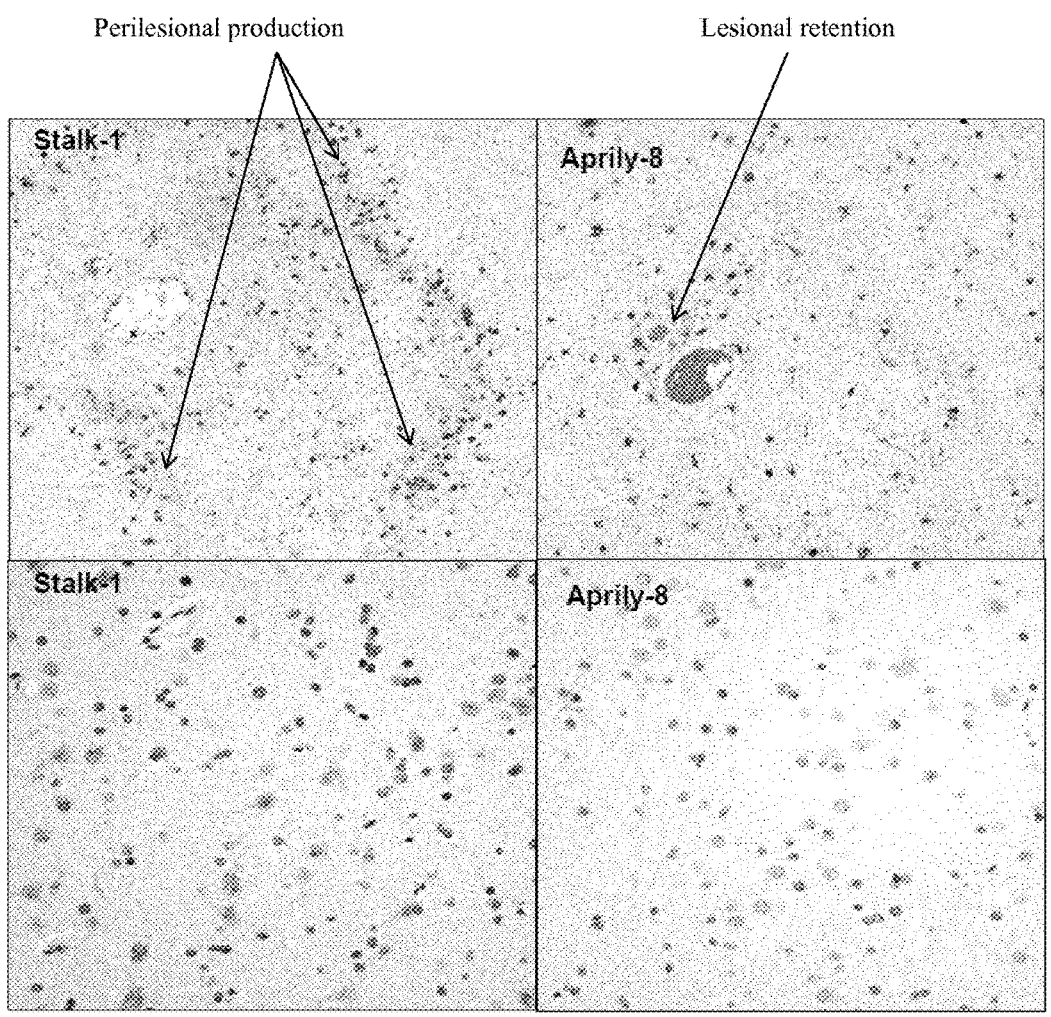
FIG. 2 represents serial sections of Multiple Sclerosis (upper panel) and Parkinson disease (bottom panel) lesions immunostained with Stalk-1 and Aprily-8.

By contrast, APRIL expression has not been detected in non-inflammatory disorders such as Parkinson diseases (FIG. 2, bottom panel).

This pattern of APRIL expression has been observed in a majority of multiple sclerosis patients (16/17) with a trend towards expression in progressive and/or acute forms of the disease (see below the Table 1).

| cases | Stalk-1 | Aprily-8 | type |
|---|---|---|---|
| 1 | − | − | RRMS |
| 2 | − | − | RRMS |
| 3 | + | + | SPMS |
| 4 | + | + | SPMS |
| 5 | + | + | PPMS |
| 6 | + | + | SPMS |
| 7 | + | ++ | acute |
| 8 | + | ++ | PPMS |
| 9 | + | +++ | PPMS |
| 10 | + | ++ | acute |
| 11 | + | ++ | PPMS |
| 12 | + | ++ | SPMS |
| 13 | + | ++ | PPMS |
| 14 | ++ | ++ | SPMS |
| 15 | ++ | ++ | acute |
| 16 | ++ | ++ | acute |
| 17 | +++ | ++ | acute |

"RR" means "relapsing remitting"
"PP" means "primary progressive"
"SP" means "secondary progressive"
"−" means that the antibodies Stalk-1 and Aprily-8 do not react with APRIL protein.

2. Two-Color Immunohistofluorescence (Stalk-1/Anti-CD68_Anti-GFAP/Aprily-8)

Material & Methods

Serial sections from biopsy of the same MS patient (as previously mentioned) was immunostained with Stalk-1 (rabbit polyclonal antibody) and an anti-CD68 (macrophage/microglial-specific mouse antibody) (upper panel).

The same biopsy was immunostained with an anti-GFAP (astrocyte-specific rabbit polyclonal antibody) and Aprily-8 (mouse antibody) (bottom panel).

Tissues were washed and binding was detected with an alexa488-conjugated anti-rabbit serum (green) and a phycoerythrin-conjugated anti-mouse serum (red).

Fluorescence was analyzed with an Axiocam microscope (Carl Zeiss).

Single and merged pictures are shown.

Nuclear (DAPI) staining is shown in the merge pictures.

Results

Figure 3:
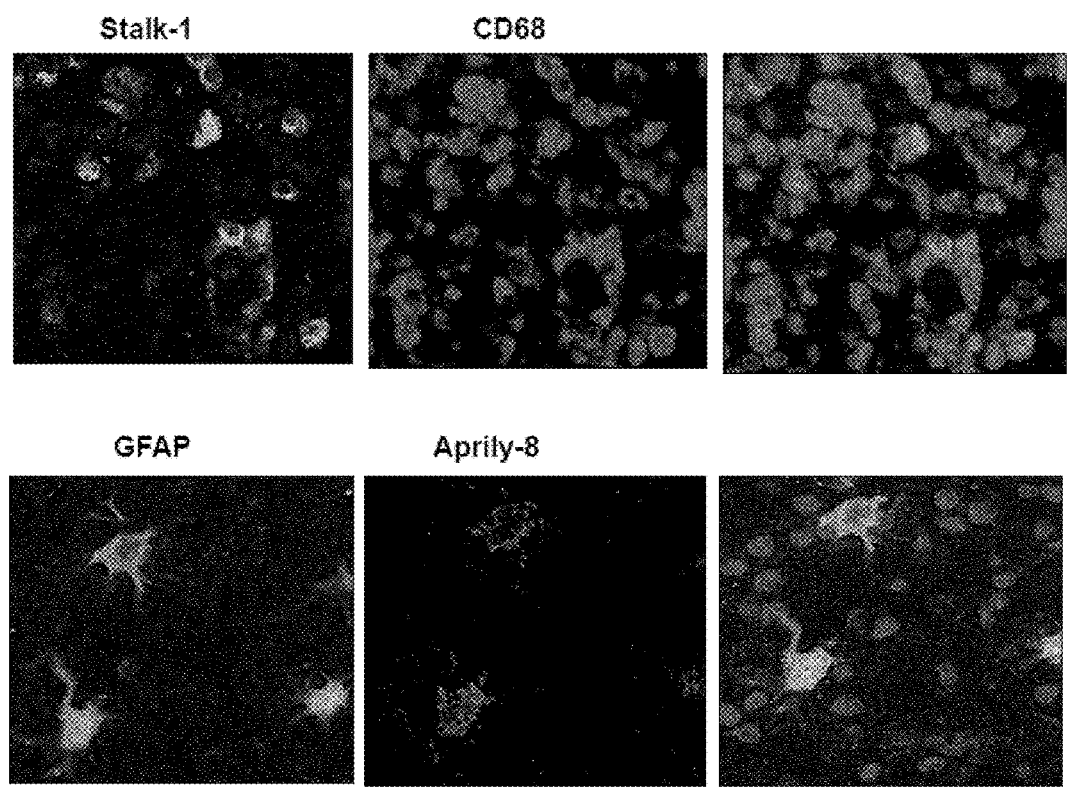
FIG. 3 represents serial sections of one representative Multiple Sclerosis lesion immunostained for Stalk-1/CD68 (upper panel) and GFAP/Aprily-8 (bottom panel).

Unlike what has been reported (Reference[13] for example), in the lesions of multiple sclerosis, APRIL is produced by a subset of CD68+ cells that could be either microglia or infiltrating macrophages, and the secreted product from these cells binds specifically onto surrounding reactive astrocytes (FIG. 3).

The conclusion of the prior art claiming APRIL production by astrocytes in MS is misleading. In fact, it seems that the authors of reference[13] used the monoclonal antibody against secreted APRIL used in the present invention, obtained an identical staining on reactive astrocytes, but misconcluded on the cellular source of APRIL.

Thus, CD[68+] cells are cells which express the Cluster of Differentiation 68.

GFAP is a Glial Fibrilary Acidic Protein which is expressed by the astrocytes.

3. Immunohistochemistry (Aprily-8)

Material & Method

A biopsy from a MS patient (as previously mentioned) was immunostained with Aprily-8 (2 µg/ml, mouse IgG1 recognizing the secreted form of human APRIL).

Tissues were washed, and incubated with a biotin-conjugated mouse Ig antiserum (available at Thermo Fisher Scientific, Inc.).

Tissues were washed, and incubated with horse raddish peroxidase (HRP)-conjugated streptavidin (available at Thermo Fisher Scientific, Inc.)

Tissue were washed and incubated with the HRP substrate amino ethyl courmarin. Light microscopy was analyzed with an Axiocam microscope (provided by Carl Zeiss).

Results

Secreted APRIL is retained by astrocytes present in lesions but also by the surrounding extracellular matrix rich in chondroitin sulfate proteoglycan (CSPG) (FIG. 9).

This also confirms the results of FIG. 2 and FIG. 3.

Example 2: Role of APRIL in Multiple Sclerosis (MS)

Plasmocytes have not been observed in the lesions used to stain for APRIL (CD138 staining, data not shown).

The Multiple Sclerosis lesions used were also devoid of ectopic germinal centers reported by others[19].

Altogether, this indicates that APRIL may play locally a new unpreviously described role in Multiple Sclerosis.

To elucidate the putative function of APRIL in Multiple Sclerosis, experimental autoimmune encephalitis (EAE) are performed in C57Bl/6 mice.

Material & Methods

EAE was induced by $MOG_{35-55}$ peptide immunization in wild-type mice (WT) or mice genetically deficient in APRIL (APRIL KO (knock-out) C57Bl/6 mice.

Wild type and APRIL-deficient C57Bl/6 mice were vaccinated against the MOG peptide$_{35-55}$ to induce a MOG-specific CD8+ T cell autoimmune responses. Clinical score and neuropathy-induced death were monitored. At the peak of the disease, spleens were harvested, dissociated, and total splenocytes were stimulated by increasing concentrations of the MOG peptide. Proliferation was assessed three days later by tritiated thymidine incorporation. * $p<0.01$ Results The clinical score (left panel) and death induced by EAE pathologies (right panel) are shown in FIG. 4.

The results show that in mice genetically deficient in APRIL the clinical EAE score was increased: for example at 19 days, the clinical score is 2 with the wild-type mice (WT) and 3 with the APRIL KO C57Bl/6 mice (APRIL KO).

The results also show that the percent death of mouse death induced by EAE associated pathologies is increased in mice genetically deficient in APRIL: for example at 20 days, the percentage is 11% for the wild-type mice (WT) and 40% for APRIL KO C57Bl/6 mice (APRIL KO).

Moreover, in this experiment, no differences in proportion and number of immune cells (myeloid, B and T cells) present in the periphery (spleen and bone marrow) and the affected spinal cord have been detected.

There was also no difference in the immunological responses between the two mice groups induced against the MOG peptide used for animal priming (splenic T-cell proliferation, FIG. 5). This absence of immunological differences is not a big surprise, since a T-cell immune response is induced by MOG peptide immunization, and APRIL role focuses on B-cell responses[8].

This suggests that APRIL may be implicated in a neuroprotective pathway.

Example 3: Treatment of Multiple Sclerosis (MS) with APRIL

Experimental Autoimmune Encephalitis (EAE) is an accepted murine model for human MS[20].

Material & Methods

EAE was induced at day 0 in 8 weeks female C57Bl/6 mice by injecting subcutaneously in both flanks 0.1 ml of an emulsion composed of 1 volume of complete Freund's adjuvant (available at Sigma) supplemented with 4 mg/ml of a *Mycobacterium Tuberculosis* lysate (available at Difco Laboratories) and 1 volume of 2.5 mg/ml of peptide 35-55 from the rat myelin oligodendrocyte glycoprotein (available at PolyPeptide Group).

Immediately after, 500 ng of *Bordetella Pertussis* toxin in PBS was injected intraperitoneally. Toxin injection was repeated on day 1.

The clinical score was evaluated as followed:
0: no sign
1: limp tail
2: limp tail associated to walking disability without any limb paralysis
3: limp tail and partial hind limb paralysis
4: limp tail and complete hind limb paralysis
5: limp tail, complete hind limb paralysis and partial anterior limb paralysis
6: moribund state conducting to animal sacrifice Mice suffering from EAE with a clinical score of 2 were treated by intravenous injections of 50 µg of Fc-APRIL $A_{88}$ in PBS every other day.

Results

APRIL treatment induces a decline in the clinical score of EAE Mice (FIG. 11).

Consequently, APRIL treatment may inhibit the neurodegenerative process occurring during MS?

Example 4: Determination of APRIL Receptor(s) on Astrocytes

Material & Methods

CRT-MG astrocytes were immunostained with Fc-control and Fc-APRIL, then analysed by flow cytometry.

CRT-MG astrocytes were immunostained with Fc-APRIL $A_{88}$ (1 µg/ml, bold lines) or control Fas-Fc (1 µg/ml, thin lines) for 30 minutes at 4 C in PBS 1% BSA.

Cells were washed, and incubated with Alexa488-conjugated human Ig antiserum for another 30 mn at 4 C.

Cells were washed again, resuspended in PBS and fluorescence was analyzed with the LSRII Becton Dickinson flow cytometer.

CRT-MG is a human astrocyte cell line.

Results

Overlayed histogram plots are shown.

The thin lines represent CRT-MG astrocytes immunostained with Fc-control.

The bold lines represent CRT-MG astrocytes immunostained with Fc-APRIL.

The results confirm in vitro binding of a soluble form of APRIL (April $A_{88}$) onto the human astrocyte cells CRT (FIG. 6).

Example 5: APRIL Bind to CSPG

Material & Methods

CRT-MG astrocytes were immunostained with 50 µl of supernatant conditioned by 293-T cells mock transfected (control supernatant) or transfected with Flag-tagged mega-APRIL $A_{88}$ (APRIL).

APRIL was pre-incubated 15 minutes at 4° C. in medium alone or with 200 µg/ml of CSPG type B (available at Sigma) before being added onto cells.

Cells were washed and incubated with an anti Flag (1 µg/ml, clone M2, available at Sigma) conjugated to biotin for 30 minutes at 4° C.

Cells were washed and incubated with streptavidin conjugated to phycoerythrin (1/300, available at Becton Dickinson).

Cells were washed, resuspended in PBS and analyzed by flow cytometry.

Results

Overlayed histograms are shown.

Grey line corresponds to control.

Black line corresponds to APRIL.

Black dashed line corresponds to APRIL pre-incubated with CSPG.

The results confirm that the inhibition mediated by CSPG (Chondroitin Sulfate ProteoGlycan) revealed the capacity of APRIL to interact with CSPG (FIG. 10).

Example 6: APRIL Recombinant Forms to be Tested

Several forms of recombinant APRIL are planned to be tested.

Indeed, APRIL has a domain binding to HSPG. HSPG acts as coreceptor ensuring oligomerization of soluble APRIL to optimally signal via APRIL known receptors (TACI and BCMA). HSPG binding may trap the injected recombinant APRIL at undesired places, such as endothelial cells lining blood vessels. This has been already observed with other HSPG-binding recombinant proteins.

Hence, recombinant natural APRIL with or without the HSPG biding domain will be tested.

Recombinant natural APRIL with or without the HSPG biding domain are shown in FIG. 7.

Sequence FLAG can be used for the purification step and does not belong to the active protein or the active fragment of the protein according to the present invention.

In the case a recombinant form without the HSPG binding domain is retained, an artificially oligomerize recombinant soluble APRIL with fusion partners may needed (see FIG. 8).

As explained below, the sequence FLAG can be used for the purification step and does not belong to the active protein or the active fragment of the protein according to the present invention.

The two fusions partners retained for the study are a constant part of a human immunoglobulin (Fc) and the headless portion of the adipocyte complement related protein of 30 kDa (ACRP30). This latter chimeric APRIL is called Mega-APRIL.

Generation of Fc- and Mega-recombinant proteins have been described in Holler N., et al., Molecular and Cellular Biology, February 2003, p. 1428-1440.

Both chimeric molecules have been shown to signal via TACI and BCMA in the absence of the HSPG binding domain.

Example 7: Best Injection Route for Recombinant APRIL

Pursuant to the results of Example 2 and Example 3, the best injection route for recombinant APRIL to distribute in brain lesions from EAE mice is tested.

After technetium labeling, 50 µg of the different recombinant forms of APRIL are injected in EAE mice. The recombinant forms of APRIL used are notably the forms described in example 6.

In vivo distribution of recombinant APRIL is monitored non-invasively by nuclear imaging, followed by invasive immunohistochemistry to localize the binding of recombinant APRIL in mouse brain lesions.

Three different routes are tested: intravenous, intranasal and intracerebroventricular.

Once the best route for APRIL brain biodistribution is determined, EAE mice are treated before disease induction (mice harboring a clinical score of 0), and once the disease is induced (mice harboring a clinical score of 1-2) 0.1 mg/kg, 1 mg/kg, and 10 mg/kg of recombinant APRIL are injected every two, three and seven days.

Daily evolution of the clinical score in treated mice is monitored.

For treated mice having recovered from EAE and showing a stable low clinical score over a week, disease reinduction is performed (according to the same protocol as induction described in Example 2 and in Example 3. The subsequent increase in the clinical score is followed daily.

This test permits to determine whether APRIL treatment during the primary disease phase is able to diminish secondary phases, knowing that human MS is a chronic progressive disease.

REFERENCES

1 Levesque, M. C. Translational Mini-Review Series on B Cell-Directed Therapies: Recent advances in B cell-directed biological therapies for autoimmune disorders. *Clin Exp Immunol* 157, 198-208, doi:CEI3979 [pii] 10.1111/j.1365-2249.2009.03979.x (2009).

2 Weber, M. S., Hemmer, B. & Cepok, S. The role of antibodies in multiple sclerosis. *Biochimica et biophysica acta* 1812, 239-245, doi: 10.1016/j.bbadis.2010.06.009 (2011).

3 Castillo-Trivino, T., Braithwaite, D., Bacchetti, P. & Waubant. E. Rituximab in relapsing and progressive forms of multiple sclerosis: a systematic review. *PLoS One* 8, e66308, doi:10.1371/journal.pone.0066308 (2013).

4 Matthes, T. et al. Production of the plasma-cell survival factor a proliferation-inducing ligand (APRIL) peaks in myeloid precursor cells from human bone marrow. *Blood* 118, 1838-1844, doi:10.1182/blood-2011-01-332940 (2011).

Huard, B. et al. APRIL secreted by neutrophils binds to heparan sulfate proteoglycans to create plasma cell niches in human mucosa. *J. Clin Invest* 118, 2887-2895, doi: 10.1172/JCI33760 (2008).

6 Hahne, M. et al. APRIL, a new ligand of the tumor necrosis factor family, stimulates tumor cell growth. *J Exp Med* 188, 1185-1190 (1998).

7 Marsters, S. A. et al. Interaction of the TNF homologues BLyS and APRIL with the TNF receptor homologues BCMA and TACI. *Curr Biol* 10, 785-788 (2000).

8 Mackay, F., Schneider, P., Rennert, P. & Browning, J. BAFF AND APRIL: a tutorial on B cell survival. *Annu Rev Immunol* 21, 231-264 (2003).

9 Schwaller, J. et al. Neutrophil-derived APRIL concentrated in tumor lesions by proteoglycans correlates with human B-cell lymphoma aggressiveness. *Blood* 109, 331-338 (2007).

Ingold, K. et al. Identification ofproteoglycans as the APRIL-specific binding partners. *J Exp Med* 201, 1375-1383 (2005).

11 Kimberley, F. C. et al. The proteoglycan (heparan sulfate proteoglycan) binding domain of APRIL serves as a platform for ligand multimerization and cross-linking. *FASEB J* 23, 1584-1595, doi:fj.08-124669 [pii]10.1096/fj.08-124669 (2009).

12 Piazza, F. et al. Cerebrospinal fluid levels of BAFF and APRIL in untreated multiple sclerosis. *Journal of neuroimmunology* 220, 104-107, doi:10.1016/j.jneuroim.2010.01.011 (2010).

13 Thangarajh, M., Masterman, T., Hillert, J., Moerk, S. & Jonsson, R. A proliferation-inducing ligand (APRIL) is expressed by astrocytes and is increased in multiple sclerosis. *Scand J Immunol* 65, 92-98, doi:SJI1867 [pii] 10.1111/j.1365-3083.2006.01867.x (2007).

14 Freeman, M. R. & Rowitch, D. H. Evolving concepts of gliogenesis: a look way back and ahead to the next 25 years. *Neuron* 80, 613-623, doi:10.1016/j.neuron.2013.10.034 (2013).

Huntington, N. D. et al. A BAFF antagonist suppresses experimental autoimmune encephalomyelitis by targeting cell-mediated and humoral immune responses. *International immnology* 18, 1473-1485, doi:10.1093/intimm/dx1080 (2006).

16 Jagessar, S. A. et al. Antibodies against human BLyS and APRIL attenuate EAE development in marmoset monkeys. *Journal of neuroinmmune pharmacology: the official journal of the Society on NeuroImmune Pharmacology* 7, 557-570, doi:10.1007/s11481-012-9384-x (2012).

17 Hartung, H. P. & Kieseier, B. C. Atacicept: targeting B cells in multiple sclerosis. *Therapeutic advances in neurological disorders* 3, 205-216, doi:10.1177/1756285610371146 (2010).

18 Lopez-Fraga, M., Fernandez, R., Albar, J. P. & Hahne, M. Biologically active APRIL is secreted following intracellular processing in the Golgi apparatus by furin convertase. *EMBO Rep* 2, 945-951 (2001).

19 Corcione, A. et al. B-cell differentiation in the CNS of patients with multiple sclerosis. *Autoimmunity reviews* 4, 549-554, doi: 10.1016/j.autrev.2005.04.012 (2005).

20 Robinson A P, Harp C T, Noronha A, Miller S D. The experimental autoimmune encephalomyelitis (EAE) model of M S: utility for understanding disease pathophysiology and treatment. Handbook of clinical neurology. 2014; 122:173-89.

21 Siebert J R, Conta Steencken A, Osterhout D J. Chondroitin sulfate proteoglycans in the nervous system: inhibitors to repair. BioMed research international. 2014; 2014:845323.

The invention claimed is:

1. A method of interfering with an antiregenerative process mediated by Chondroitin Sulfate ProteoGlycans (CSPG) comprising administering to a subject in need thereof a composition comprising an active substance which comprises or consists of:
a protein comprising one of the amino acid sequences of SEQ ID NO: 1, SEQ ID NO: 2, or SEQ ID NO:3, representing the APRIL protein.

2. The method according to claim 1, wherein the protein of the composition is a chimeric protein consisting of an oligomer of the protein of one of the amino acid sequences of SEQ ID NO: 1 or SEQ ID NO: 2 or SEQ ID NO:3, each protein of the oligomer being linked to another protein of the oligomer by a constant region of an immunoglobulin of an amino acid sequence of SEQ ID NO: 9 or SEQ ID NO: 10.

3. The method according to claim 1, wherein the protein of the composition is a chimeric protein consisting of an oligomer of the protein of one of the amino acid sequences of SEQ ID NO: 1 or SEQ ID NO: 2 or SEQ ID NO:3, each protein of the oligomer being linked to the headless region of an ACRP30 protein of an amino acid sequence of SEQ ID NO: 7 or SEQ ID NO: 8.

4. The method according to claim 1, wherein the active substance of the composition forms a complex with an astrocyte and/or to CSPG, the active substance being:

(i) the amino acid sequence of SEQ ID NO: 1 or SEQ ID NO: 2 or SEQ ID NO: 3, or (ii) a chimeric protein consisting of an oligomer of the protein of one of the amino acid sequences of SEQ ID NO: 1 or SEQ ID NO: 2 or SEQ ID NO:3, each protein of the oligomer being linked to another protein of the oligomer by a constant region of an immunoglobulin of an amino acid sequence of SEQ ID NO: 9 or SEQ ID NO: 10, or (iii) a chimeric protein consisting of an oligomer of the protein of one of the amino acid sequences of SEQ ID NO: 1 or SEQ ID NO: 2 or SEQ ID NO:3, each protein of the oligomer being linked to the headless region of an ACRP30 protein of an amino acid sequence of SEQ ID NO: 7 or SEQ ID NO: 8.

5. A method for treating multiple sclerosis or autoimmune encephalitis, said method comprising administering to a subject in need thereof an effective amount of a composition comprising an active substance which comprises or consists of:
a protein comprising one of the amino acid sequences of SEQ ID NO: 1 or SEQ ID NO: 2 or SEQ ID NO:3, representing the APRIL protein.

* * * * *

SEQUENCE LISTING

```
<160> NUMBER OF SEQ ID NOS: 17

<210> SEQ ID NO 1
<211> LENGTH: 136
<212> TYPE: PRT
```

<213> ORGANISM: Homo Sapiens

<400> SEQUENCE: 1

```
His Ser Val Leu His Leu Val Pro Ile Asn Ala Thr Ser Lys Asp
1               5                   10                  15

Ser Asp Val Thr Glu Val Met Trp Gln Pro Ala Leu Arg Arg Gly Arg
            20                  25                  30

Gly Leu Gln Ala Gln Gly Tyr Gly Val Arg Ile Gln Asp Ala Gly Val
        35                  40                  45

Tyr Leu Leu Tyr Ser Gln Val Leu Phe Gln Asp Val Thr Phe Thr Met
    50                  55                  60

Gly Gln Val Val Ser Arg Glu Gly Gln Gly Arg Gln Glu Thr Leu Phe
65                  70                  75                  80

Arg Cys Ile Arg Ser Met Pro Ser His Pro Asp Arg Ala Tyr Asn Ser
                85                  90                  95

Cys Tyr Ser Ala Gly Val Phe His Leu His Gln Gly Asp Ile Leu Ser
                100                 105                 110

Val Ile Ile Pro Arg Ala Arg Ala Lys Leu Asn Leu Ser Pro His Gly
            115                 120                 125

Thr Phe Leu Gly Phe Val Lys Leu
        130                 135
```

<210> SEQ ID NO 2
<211> LENGTH: 146
<212> TYPE: PRT
<213> ORGANISM: Homo Sapiens

<400> SEQUENCE: 2

```
Ala Val Leu Thr Gln Lys Gln Lys Gln His Ser Val Leu His Leu
1               5                   10                  15

Val Pro Ile Asn Ala Thr Ser Lys Asp Asp Ser Asp Val Thr Glu Val
            20                  25                  30

Met Trp Gln Pro Ala Leu Arg Arg Gly Arg Gly Leu Gln Ala Gln Gly
        35                  40                  45

Tyr Gly Val Arg Ile Gln Asp Ala Gly Val Tyr Leu Leu Tyr Ser Gln
    50                  55                  60

Val Leu Phe Gln Asp Val Thr Phe Thr Met Gly Gln Val Val Ser Arg
65                  70                  75                  80

Glu Gly Gln Gly Arg Gln Glu Thr Leu Phe Arg Cys Ile Arg Ser Met
                85                  90                  95

Pro Ser His Pro Asp Arg Ala Tyr Asn Ser Cys Tyr Ser Ala Gly Val
                100                 105                 110

Phe His Leu His Gln Gly Asp Ile Leu Ser Val Ile Ile Pro Arg Ala
            115                 120                 125

Arg Ala Lys Leu Asn Leu Ser Pro His Gly Thr Phe Leu Gly Phe Val
        130                 135                 140

Lys Leu
145
```

<210> SEQ ID NO 3
<211> LENGTH: 233
<212> TYPE: PRT
<213> ORGANISM: Homo Sapiens

<400> SEQUENCE: 3

```
Met Gly Gly Pro Val Arg Glu Pro Ala Leu Ser Val Ala Leu Trp Leu
1               5                   10                  15
```

Ser Trp Gly Ala Ala Leu Gly Ala Val Ala Cys Ala Met Ala Leu Leu
            20                  25                  30

Thr Gln Gln Thr Glu Leu Gln Ser Leu Arg Arg Glu Val Ser Arg Leu
        35                  40                  45

Gln Gly Thr Gly Gly Pro Ser Gln Asn Gly Glu Gly Tyr Pro Trp Gln
    50                  55                  60

Ser Leu Pro Glu Gln Ser Ser Asp Ala Leu Glu Ala Trp Glu Asn Gly
65                  70                  75                  80

Glu Arg Ser Arg Lys Arg Arg Ala Val Leu Thr Gln Lys Gln Lys Lys
                85                  90                  95

Gln His Ser Val Leu His Leu Val Pro Ile Asn Ala Thr Ser Lys Asp
            100                 105                 110

Asp Ser Asp Val Thr Glu Val Met Trp Gln Pro Ala Leu Arg Arg Gly
        115                 120                 125

Arg Gly Leu Gln Ala Gln Gly Tyr Gly Val Arg Ile Gln Asp Ala Gly
    130                 135                 140

Val Tyr Leu Leu Tyr Ser Gln Val Leu Phe Gln Asp Val Thr Phe Thr
145                 150                 155                 160

Met Gly Gln Val Val Ser Arg Glu Gly Gln Gly Arg Gln Glu Thr Leu
                165                 170                 175

Phe Arg Cys Ile Arg Ser Met Pro Ser His Pro Asp Arg Ala Tyr Asn
            180                 185                 190

Ser Cys Tyr Ser Ala Gly Val Phe His Leu His Gln Gly Asp Ile Leu
        195                 200                 205

Ser Val Ile Ile Pro Arg Ala Arg Ala Lys Leu Asn Leu Ser Pro His
    210                 215                 220

Gly Thr Phe Leu Gly Phe Val Lys Leu
225                 230

<210> SEQ ID NO 4
<211> LENGTH: 411
<212> TYPE: DNA
<213> ORGANISM: Homo Sapiens

<400> SEQUENCE: 4
cactctgtcc tgcacctggt tcccattaac gccacctcca aggatgactc cgatgtgaca      60
gaggtgatgt ggcaaccagc tcttaggcgt gggagaggcc tacaggccca aggatatggt     120
gtccgaatcc aggatgctgg agtttatctg ctgtatagcc aggtcctgtt tcaagacgtg     180
actttcacca tgggtcaggt ggtgtctcga gaaggcaagg aaggcagga gactctattc      240 cgatgtataa gagtatgcc ctcccacccg gaccgggcct acaacagctg ctatagcgca      300
ggtgtcttcc atttacacca agggatatt ctgagtgtca taattcccg ggcaaggggcg      360 aaacttaacc tctctccaca tggaaccttc ctggggtttg tgaaactgtg a              411

<210> SEQ ID NO 5
<211> LENGTH: 441
<212> TYPE: DNA
<213> ORGANISM: Homo Sapiens

<400> SEQUENCE: 5
gcagtgctca cccaaaaaca gaagaagcag cactctgtcc tgcacctggt tcccattaac      60
gccacctcca aggatgactc cgatgtgaca gaggtgatgt ggcaaccagc tcttaggcgt     120
gggagaggcc tacaggccca aggatatggt gtccgaatcc aggatgctgg agtttatctg    180

```
ctgtatagcc aggtcctgtt tcaagacgtg actttcacca tgggtcaggt ggtgtctcga      240
gaaggccaag gaaggcagga gactctattc cgatgtataa gaagtatgcc ctcccacccg      300
gaccgggcct acaacagctg ctatagcgca ggtgtcttcc atttacacca agggatatt      360 ctgagtgtca taattccccg ggcaagggcg aaacttaacc tctctccaca tggaaccttc      420
ctggggtttg tgaaactgtg a                                                 441

<210> SEQ ID NO 6
<211> LENGTH: 702
<212> TYPE: DNA
<213> ORGANISM: Homo Sapiens

<400> SEQUENCE: 6
atggggggcc cagtcagaga gccggcactc tcagttgccc tctggttgag ttgggggca       60 gctctggggg ccgtggcttg tgccatggct ctgctgaccc aacaaacaga gctgcagagc     120
ctcaggagag aggtgagccg gctgcagggg acaggaggcc cctcccagaa tggggaaggg     180
tatccctggc agagtctccc ggagcagagt tccgatgccc tggaagcctg ggagaatggg     240
gagagatccc ggaaaaggag agcagtgctc acccaaaaac agaagaagca gcactctgtc     300
ctgcacctgg ttcccattaa cgccacctcc aaggatgact ccgatgtgac agaggtgatg     360
tggcaaccag ctcttaggcg tgggagaggc ctacaggccc aaggatatgg tgtccgaatc     420
caggatgctg agtttatct gctgtatagc caggtcctgt ttcaagacgt gactttcacc     480
atgggtcagg tggtgtctcg agaaggccaa ggaaggcagg agactctatt ccgatgtata     540
agaagtatgc cctcccaccc ggaccgggcc tacaacagct gctatagcgc aggtgtcttc     600
catttacacc aagggatat ctgagtgtc ataattcccc gggcaagggc gaaacttaac       660
ctctctccac atggaacctt cctggggttt gtgaaactgt ga                         702

<210> SEQ ID NO 7
<211> LENGTH: 239
<212> TYPE: PRT
<213> ORGANISM: Artificial sequence
<220> FEATURE:
<223> OTHER INFORMATION: chimeric protein

<400> SEQUENCE: 7

His Asp Gln Glu Thr Thr Thr Gln Gly Pro Gly Val Leu Leu Pro Leu
1               5                   10                  15

Pro Lys Gly Ala Cys Thr Gly Trp Met Ala Gly Ile Pro Gly His Pro
            20                  25                  30

Gly His Asn Gly Ala Pro Gly Arg Asp Gly Arg Asp Gly Thr Pro Gly
        35                  40                  45

Glu Lys Gly Glu Lys Gly Asp Pro Gly Leu Ile Gly Pro Lys Gly Asp
    50                  55                  60

Ile Gly Glu Thr Gly Val Pro Gly Ala Glu Gly Pro Arg Gly Phe Pro
65                  70                  75                  80

Gly Ile Gln Gly Arg Lys Gly Glu Pro Gly Glu Gly Ala Ala Val Leu
                85                  90                  95

Thr Gln Lys Gln Lys Lys Gln His Ser Val Leu His Leu Val Pro Ile
            100                 105                 110

Asn Ala Thr Ser Lys Asp Asp Ser Asp Val Thr Glu Val Met Trp Gln
        115                 120                 125

Pro Ala Leu Arg Arg Gly Arg Gly Leu Gln Ala Gln Gly Tyr Gly Val
    130                 135                 140
```

Arg Ile Gln Asp Ala Gly Val Tyr Leu Leu Tyr Ser Gln Val Leu Phe
145                 150                 155                 160

Gln Asp Val Thr Phe Thr Met Gly Gln Val Val Ser Arg Glu Gly Gln
            165                 170                 175

Gly Arg Gln Glu Thr Leu Phe Arg Cys Ile Arg Ser Met Pro Ser His
        180                 185                 190

Pro Asp Arg Ala Tyr Asn Ser Cys Tyr Ser Ala Gly Val Phe His Leu
    195                 200                 205

His Gln Gly Asp Ile Leu Ser Val Ile Ile Pro Arg Ala Arg Ala Lys
210                 215                 220

Leu Asn Leu Ser Pro His Gly Thr Phe Leu Gly Phe Val Lys Leu
225                 230                 235

<210> SEQ ID NO 8
<211> LENGTH: 229
<212> TYPE: PRT
<213> ORGANISM: Artificial sequence
<220> FEATURE:
<223> OTHER INFORMATION: chimeric protein

<400> SEQUENCE: 8

His Asp Gln Glu Thr Thr Thr Gln Gly Pro Gly Val Leu Leu Pro Leu
1               5                   10                  15

Pro Lys Gly Ala Cys Thr Gly Trp Met Ala Gly Ile Pro Gly His Pro
            20                  25                  30

Gly His Asn Gly Ala Pro Gly Arg Asp Gly Arg Asp Gly Thr Pro Gly
        35                  40                  45

Glu Lys Gly Glu Lys Gly Asp Pro Gly Leu Ile Gly Pro Lys Gly Asp
50                  55                  60

Ile Gly Glu Thr Gly Val Pro Gly Ala Glu Gly Pro Arg Gly Phe Pro
65                  70                  75                  80

Gly Ile Gln Gly Arg Lys Gly Glu Pro Gly Glu Gly Ala His Ser Val
                85                  90                  95

Leu His Leu Val Pro Ile Asn Ala Thr Ser Lys Asp Asp Ser Asp Val
            100                 105                 110

Thr Glu Val Met Trp Gln Pro Ala Leu Arg Arg Gly Arg Gly Leu Gln
        115                 120                 125

Ala Gln Gly Tyr Gly Val Arg Ile Gln Asp Ala Gly Val Tyr Leu Leu
    130                 135                 140

Tyr Ser Gln Val Leu Phe Gln Asp Val Thr Phe Thr Met Gly Gln Val
145                 150                 155                 160

Val Ser Arg Glu Gly Gln Gly Arg Gln Glu Thr Leu Phe Arg Cys Ile
                165                 170                 175

Arg Ser Met Pro Ser His Pro Asp Arg Ala Tyr Asn Ser Cys Tyr Ser
            180                 185                 190

Ala Gly Val Phe His Leu His Gln Gly Asp Ile Leu Ser Val Ile Ile
        195                 200                 205

Pro Arg Ala Arg Ala Lys Leu Asn Leu Ser Pro His Gly Thr Phe Leu
    210                 215                 220

Gly Phe Val Lys Leu
225

<210> SEQ ID NO 9
<211> LENGTH: 387
<212> TYPE: PRT
<213> ORGANISM: Artificial sequence
<220> FEATURE:

<223> OTHER INFORMATION: chimeric protein

<400> SEQUENCE: 9

```
Pro Pro Cys Pro Ala Pro Glu Leu Leu Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
                35                  40                  45

Phe Asn Trp Tyr Val Asp Gly Val Glu Val His Asn Ala Lys Thr Lys
        50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys Arg Ser Pro
    210                 215                 220

Gln Pro Gln Pro Lys Pro Gln Pro Lys Pro Glu Pro Glu Gly Ser Leu
225                 230                 235                 240

Gln Ala Val Leu Thr Gln Lys Gln Lys Gln His Ser Val Leu His
                245                 250                 255

Leu Val Pro Ile Asn Ala Thr Ser Lys Asp Asp Ser Asp Val Thr Glu
            260                 265                 270

Val Met Trp Gln Pro Ala Leu Arg Arg Gly Arg Gly Leu Gln Ala Gln
        275                 280                 285

Gly Tyr Gly Val Arg Ile Gln Asp Ala Gly Val Tyr Leu Leu Tyr Ser
    290                 295                 300

Gln Val Leu Phe Gln Asp Val Thr Phe Thr Met Gly Gln Val Val Ser
305                 310                 315                 320

Arg Glu Gly Gln Gly Arg Gln Glu Thr Leu Phe Arg Cys Ile Arg Ser
                325                 330                 335

Met Pro Ser His Pro Asp Arg Ala Tyr Asn Ser Cys Tyr Ser Ala Gly
            340                 345                 350

Val Phe His Leu His Gln Gly Asp Ile Leu Ser Val Ile Ile Pro Arg
        355                 360                 365

Ala Arg Ala Lys Leu Asn Leu Ser Pro His Gly Thr Phe Leu Gly Phe
    370                 375                 380

Val Lys Leu
385
```

```
<210> SEQ ID NO 10
<211> LENGTH: 377
<212> TYPE: PRT
<213> ORGANISM: Artificial sequence
<220> FEATURE:
<223> OTHER INFORMATION: chimeric protein

<400> SEQUENCE: 10

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
        35                  40                  45

Phe Asn Trp Tyr Val Asp Gly Val Glu Val His Asn Ala Lys Thr Lys
    50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys Arg Ser Pro
    210                 215                 220

Gln Pro Gln Pro Lys Pro Gln Pro Lys Pro Glu Pro Glu Gly Ser Leu
225                 230                 235                 240

Gln His Ser Val Leu His Leu Val Pro Ile Asn Ala Thr Ser Lys Asp
                245                 250                 255

Asp Ser Asp Val Thr Glu Val Met Trp Gln Pro Ala Leu Arg Arg Gly
            260                 265                 270

Arg Gly Leu Gln Ala Gln Gly Tyr Gly Val Arg Ile Gln Asp Ala Gly
        275                 280                 285

Val Tyr Leu Leu Tyr Ser Gln Val Leu Phe Gln Asp Val Thr Phe Thr
    290                 295                 300

Met Gly Gln Val Val Ser Arg Glu Gly Gln Gly Arg Gln Glu Thr Leu
305                 310                 315                 320

Phe Arg Cys Ile Arg Ser Met Pro Ser His Pro Asp Arg Ala Tyr Asn
                325                 330                 335

Ser Cys Tyr Ser Ala Gly Val Phe His Leu His Gln Gly Asp Ile Leu
            340                 345                 350

Ser Val Ile Ile Pro Arg Ala Arg Ala Lys Leu Asn Leu Ser Pro His
        355                 360                 365
```

```
Gly Thr Phe Leu Gly Phe Val Lys Leu
        370                 375
```

<210> SEQ ID NO 11
<211> LENGTH: 93
<212> TYPE: PRT
<213> ORGANISM: Homo Sapiens

<400> SEQUENCE: 11

```
His Asp Gln Glu Thr Thr Thr Gln Gly Pro Gly Val Leu Leu Pro Leu
1               5                   10                  15

Pro Lys Gly Ala Cys Thr Gly Trp Met Ala Gly Ile Pro Gly His Pro
            20                  25                  30

Gly His Asn Gly Ala Pro Gly Arg Asp Gly Arg Asp Gly Thr Pro Gly
        35                  40                  45

Glu Lys Gly Glu Lys Gly Asp Pro Gly Leu Ile Gly Pro Lys Gly Asp
    50                  55                  60

Ile Gly Glu Thr Gly Val Pro Gly Ala Glu Gly Pro Arg Gly Phe Pro
65                  70                  75                  80

Gly Ile Gln Gly Arg Lys Gly Glu Pro Gly Glu Gly Ala
                85                  90
```

<210> SEQ ID NO 12
<211> LENGTH: 221
<212> TYPE: PRT
<213> ORGANISM: Homo Sapiens

<400> SEQUENCE: 12

```
Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
        35                  40                  45

Phe Asn Trp Tyr Val Asp Gly Val Glu Val His Asn Ala Lys Thr Lys
    50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220
```

<210> SEQ ID NO 13
<211> LENGTH: 20
<212> TYPE: PRT
<213> ORGANISM: Artificial sequence
<220> FEATURE:
<223> OTHER INFORMATION: linker sequence

<400> SEQUENCE: 13

Arg Ser Pro Gln Pro Gln Pro Lys Pro Gln Pro Lys Pro Glu Pro Glu
1               5                   10                  15

Gly Ser Leu Gln
            20

<210> SEQ ID NO 14
<211> LENGTH: 720
<212> TYPE: DNA
<213> ORGANISM: Artificial sequence
<220> FEATURE:
<223> OTHER INFORMATION: chimeric protein

<400> SEQUENCE: 14
catgaccagg aaaccacgac tcaagggccc ggagtcctgc ttcccctgcc caagggggcc      60
tgcacaggtt ggatggcggg catcccaggg catccgggcc ataatgggc cccaggccgt      120 gatggcagag atggcacccc tggtgagaag ggtgagaaag gagatccagg tcttattggt     180
cctaagggag acatcggtga accggagta cccggggctg aaggtccccg aggctttccg      240
ggaatccaag gcaggaaagg agaacctgga gaaggtgccg cagtgctcac ccaaaaacag     300
aagaagcagc actctgtcct gcacctggtt cccattaacg ccacctccaa ggatgactcc     360
gatgtgacag aggtgatgtg caaccagct cttaggcgtg ggagaggcct acaggcccaa      420
ggatatggtg tccgaatcca ggatgctgga gtttatctgc tgtatagcca ggtcctgttt    480
caagacgtga ctttcaccat gggtcaggtg gtgtctcgag aaggccaagg aaggcaggag    540
actctattcc gatgtataag aagtatgccc tcccacccgg accgggccta acagcagctgc   600 tatagcgcag gtgtcttcca tttacaccaa ggggatattc tgagtgtcat aattccccgg   660
gcaagggcga acttaaccct ctctccacat ggaaccttcc tggggtttgt gaaactgtga    720

<210> SEQ ID NO 15
<211> LENGTH: 690
<212> TYPE: DNA
<213> ORGANISM: Artificial sequence
<220> FEATURE:
<223> OTHER INFORMATION: chimeric protein

<400> SEQUENCE: 15
catgaccagg aaaccacgac tcaagggccc ggagtcctgc ttcccctgcc caagggggcc      60
tgcacaggtt ggatggcggg catcccaggg catccgggcc ataatgggc cccaggccgt      120 gatggcagag atggcacccc tggtgagaag ggtgagaaag gagatccagg tcttattggt     180
cctaagggag acatcggtga accggagta cccggggctg aaggtccccg aggctttccg      240
ggaatccaag gcaggaaagg agaacctgga gaaggtgccc actctgtcct gcacctggtt    300
cccattaacg ccacctccaa ggatgactcc gatgtgacag aggtgatgtg caaccagct     360 cttaggcgtg ggagaggcct acaggcccaa ggatatggtg tccgaatcca ggatgctgga    420
gtttatctgc tgtatagcca ggtcctgttt caagacgtga ctttcaccat gggtcaggtg    480
gtgtctcgag aaggccaagg aaggcaggag actctattcc gatgtataag aagtatgccc   540
tcccacccgg accgggccta acagcagctgc tatagcgcag gtgtcttcca tttacaccaa   600

```
ggggatattc tgagtgtcat aattccccgg gcaagggcga aacttaacct ctctccacat    660
ggaaccttcc tggggtttgt gaaactgtga                                    690

<210> SEQ ID NO 16
<211> LENGTH: 1227
<212> TYPE: DNA
<213> ORGANISM: Artificial sequence
<220> FEATURE:
<223> OTHER INFORMATION: chimeric protein

<400> SEQUENCE: 16
atggctatca tctacctcat cctcctgttc accgctgtgc ggggcctcga caaaactcac     60
acatgcccac cgtgcccagc acctgaactc ctggggggac cgtcagtctt cctcttcccc    120
ccaaaaccca aggacaccct catgatctcc cggacccctg aggtcacatg cgtggtggtg    180
gacgtgagcc acgaagaccc tgaggtcaag ttcaactggt acgtggacgg cgtggaggtg    240
cataatgcca agacaaagcc gcgggaggag cagtacaaca gcacgtaccg tgtggtcagc    300
gtcctcaccg tcctgcacca ggactggctg aatggcaagg agtacaagtg caaggtctcc    360
aacaaagccc tcccagcccc catcgagaaa accatctcca aagccaaagg cagccccga    420 gaaccacagg tgtacaccct gcccccatcc cgggatgagc tgaccaagaa ccaggtcagc    480
ctgacctgcc tggtcaaagg cttctatccc agcgacatcg ccgtggagtg ggagagcaat    540
gggcagccgg agaacaacta caagaccacg cctcccgtgt ggactccga cggctccttc    600 ttcctctaca gcaagctcac cgtggacaag agcaggtggc agcaggggaa cgtcttctca    660
tgctccgtga tgcatgaggc tctgcacaac cactacacgc agaagagcct ctccctgtct    720
ccgggtaaaa gatctccgca gccgcagccg aaaccgcagc cgaaaccgga accggaagga    780
tccctgcagg cagtgctcac ccaaaaacag aagaagcagc actctgtcct gcacctggtt    840
cccattaacg ccacctccaa ggatgactcc gatgtgacag aggtgatgtg caaccagct    900 cttaggcgtg ggagaggcct acaggcccaa ggatatggtg tccgaatcca ggatgctgga    960
gtttatctgc tgtatagcca ggtcctgttt caagacgtga ctttcaccat gggtcaggtg    1020
gtgtctcgag aaggccaagg aaggcaggag actctattcc gatgtataag aagtatgccc    1080
tcccacccgg accgggccta acagctgctgc tatagcgcag gtgtcttcca tttacaccaa    1140
ggggatattc tgagtgtcat aattccccgg gcaagggcga aacttaacct ctctccacat    1200
ggaaccttcc tggggtttgt gaaactg                                       1227

<210> SEQ ID NO 17
<211> LENGTH: 1197
<212> TYPE: DNA
<213> ORGANISM: Artificial sequence
<220> FEATURE:
<223> OTHER INFORMATION: chimeric protein

<400> SEQUENCE: 17
atggctatca tctacctcat cctcctgttc accgctgtgc ggggcctcga caaaactcac     60
acatgcccac cgtgcccagc acctgaactc ctggggggac cgtcagtctt cctcttcccc    120
ccaaaaccca aggacaccct catgatctcc cggacccctg aggtcacatg cgtggtggtg    180
gacgtgagcc acgaagaccc tgaggtcaag ttcaactggt acgtggacgg cgtggaggtg    240
cataatgcca agacaaagcc gcgggaggag cagtacaaca gcacgtaccg tgtggtcagc    300
gtcctcaccg tcctgcacca ggactggctg aatggcaagg agtacaagtg caaggtctcc    360
```

```
aacaaagccc tcccagcccc catcgagaaa accatctcca aagccaaagg gcagccccga    420
gaaccacagg tgtacaccct gcccccatcc cgggatgagc tgaccaagaa ccaggtcagc    480
ctgacctgcc tggtcaaagg cttctatccc agcgacatcg ccgtggagtg ggagagcaat    540
gggcagccgg agaacaacta caagaccacg cctcccgtgt tggactccga cggctccttc    600
ttcctctaca gcaagctcac cgtggacaag agcaggtggc agcaggggaa cgtcttctca    660
tgctccgtga tgcatgaggc tctgcacaac cactacacgc agaagagcct ctccctgtct    720
ccgggtaaaa gatctccgca gccgcagccg aaaccgcagc cgaaaccgga accggaagga    780
tccctgcagc actctgtcct gcacctggtt cccattaacg ccacctccaa ggatgactcc    840
gatgtgacag aggtgatgtg gcaaccagct cttaggcgtg ggagaggcct acaggcccaa    900
ggatatggtg tccgaatcca ggatgctgga gtttatctgc tgtatagcca ggtcctgttt    960
caagacgtga ctttcaccat gggtcaggtg gtgtctcgag aaggccaagg aaggcaggag   1020
actctattcc gatgtataag aagtatgccc tcccacccgg accgggccta caacagctgc   1080
tatagcgcag gtgtcttcca tttacaccaa ggggatattc tgagtgtcat aattccccgg   1140
gcaagggcga aacttaacct ctctccacat ggaaccttcc tggggtttgt gaaactg      1197
```